(12) United States Patent
Zayas

(10) Patent No.: US 12,428,684 B2
(45) Date of Patent: Sep. 30, 2025

(54) METHODS FOR DETECTING AND TREATING A TUMORIGENIC PHENOTYPE OF THE LIVER

(71) Applicant: Active Genomes Expressed Diagnostics Corp, Washington, DC (US)

(72) Inventor: Rachel Zayas, Washington, DC (US)

(73) Assignee: Active Genomes Expressed Diagnostics Corp, Bethesda, MD (US)

( * ) Notice: Subject to any disclaimer, the term of this patent is extended or adjusted under 35 U.S.C. 154(b) by 946 days.

(21) Appl. No.: 17/257,370

(22) PCT Filed: Jul. 5, 2019

(86) PCT No.: PCT/US2019/040695
§ 371 (c)(1),
(2) Date: Dec. 31, 2020

(87) PCT Pub. No.: WO2020/010311
PCT Pub. Date: Jan. 9, 2020

(65) Prior Publication Data
US 2023/0026916 A1    Jan. 26, 2023

Related U.S. Application Data

(60) Provisional application No. 62/694,325, filed on Jul. 5, 2018.

(51) Int. Cl.
C12Q 1/68 (2018.01)
C12P 19/34 (2006.01)
C12Q 1/6886 (2018.01)
C12Q 1/6869 (2018.01)

(52) U.S. Cl.
CPC ......... *C12Q 1/6886* (2013.01); *C12Q 1/6869* (2013.01); *C12Q 2600/154* (2013.01); *C12Q 2600/158* (2013.01); *C12Q 2600/178* (2013.01)

(58) Field of Classification Search
CPC ................................................... C12Q 1/6886
See application file for complete search history.

(56) References Cited

U.S. PATENT DOCUMENTS

| | | | |
|---|---|---|---|
| 9,840,742 B2 | 12/2017 | Song et al. | |
| 2007/0161031 A1 | 7/2007 | Trinklein et al. | |
| 2011/0151460 A1 | 6/2011 | Klass et al. | |
| 2011/0244465 A1 | 10/2011 | Harvey et al. | |
| 2012/0238463 A1* | 9/2012 | Goel | C12Q 1/6886 506/7 |
| 2014/0350071 A1* | 11/2014 | Sehgal | A61P 11/00 435/375 |
| 2015/0011403 A1* | 1/2015 | Lo | C12Q 1/6881 702/20 |
| 2016/0145683 A1 | 5/2016 | Fan et al. | |
| 2017/0175200 A1 | 6/2017 | Lyden et al. | |
| 2017/0175205 A1* | 6/2017 | Toung | G16B 40/00 |
| 2018/0149636 A1* | 5/2018 | Lo | G16B 20/00 |
| 2018/0274039 A1* | 9/2018 | Zhang | C12Q 1/6886 |
| 2020/0308651 A1* | 10/2020 | De Carvalho | C12Q 1/6827 |
| 2021/0156863 A1* | 5/2021 | Dinz De Carvalho | G16B 20/00 |
| 2021/0404007 A1* | 12/2021 | Zhou | C12Q 1/6886 |

FOREIGN PATENT DOCUMENTS

| | | |
|---|---|---|
| WO | WO-2005106044 A1 | 11/2005 |
| WO | 2014124527 A1 | 8/2014 |
| WO | 2015131153 A1 | 9/2015 |
| WO | 2017180499 A2 | 10/2017 |
| WO | WO-2020010311 A2 | 1/2020 |
| WO | WO-2020087037 A2 | 4/2020 |
| WO | WO-2023010129 A2 | 2/2023 |

OTHER PUBLICATIONS

Sun et al., "High-Resolution Enzymatic Mapping of Genomic 5-Hydroxymethylcytosine in Mouse Embryonic Stem Cells," Cell Reports, 2013, vol. 3, pp. 567-576, The Authors, Cell Press, Cambridge, Massachusetts.

Takashima et al., "Targeting the RAS oncogene," Expert Opinion on Therapeutic Targets, 2013, vol. 17(5), pp. 507-531, Informa, London, United Kingdom.

Tang et al., "Tumor origin detection with tissue-specific miRNA and DNA methylation markers," Bioinformatics, 2018, vol. 34(3), pp. 398-406, Oxford University Press, Oxford, United Kingdom.

Tavormina, "Identification And Molecular Analysis of DNA in Exosomes," Dissertation (PhD), 2019, pp. 1-232, The University of Texas Md Anderson Cancer Center UTHealth Graduate School of Biomedical Sciences Dissertations and Theses, Houston, Texas.

Tsimbouri et al., "bcl-xL and RAG genes are induced and the response to IL-2 enhanced in EuEBNA-q transgenic mouse lymphocytes," Oncogene, 2002, vol. 21, pp. 5182-5187, Nature Publishing Group, Berlin, Germany.

(Continued)

*Primary Examiner* — Kenneth R Horlick
(74) *Attorney, Agent, or Firm* — WILSON SONSINI GOODRICH & ROSATI

(57) ABSTRACT

In an aspect, a method comprises (a) isolating cell-free DNA molecules obtained or derived from a blood sample of a subject; (b) subjecting the cfDNA molecules to TET-associated sequencing comprising: (i) using a TET enzyme to oxidize 5-mC residues and 5-hmC residues of the cfDNA molecules, (ii) sequencing the TET-converted cfDNA molecules to produce a set of cfDNA methylation sequencing reads; (c) processing the set of cfDNA methylation sequencing reads to determine a liver-specific methylation pattern of the cfDNA molecules across a set of liver-specific differentially methylated genomic regions, wherein the processing comprises distinguishing between 5-mC and 5-hmC residues and cytosine residues; (d) determining a presence of a tumorigenic phenotype of the liver, based at least in part on the determined liver-specific methylation pattern; and (e) administering a treatment to the subject to treat the tumorigenic phenotype.

16 Claims, 5 Drawing Sheets

Specification includes a Sequence Listing.

(56) References Cited

OTHER PUBLICATIONS

Unknown, "BRAF gene," Genetics Home Reference—NIH, May 2021, pp. 1-7, Retrieved from https://ghr.nlm.nih.gov/gene/BRAF#.
Unknown, "Cirrhosis," American Association for Clinical Chemistry, 2018, pp. 1-10, Retrieved from shttps://labtestsonline.org/conditions/cirrhosis.
Unknown, "Comprehensive suite of molecular biology and sequence analysis tools," Geneious Prime—Molecular Biology and Sequence Analysis Software, Aug. 2021, pp. 1-13, retrieved from: https://www.geneious.com/prime/.
Unknown, "Custom qPCR Probes," Sigma Aldrich—Primer and Probe Design, 2018, pp. 1-8, Retrieved from: https://www.sigmaaldrich.com/content/dam/sigma-aldrich/docs/SAJ/Brochure/1/j_qpcr_techguide03.pdf.
Unknown, "Focused sequencing of specific transcripts of interest," Illumina, 2018, pp. 1-5, retrieved from: https://www.illumina.com/techniques/sequencing/rna-sequencing/targeted-rna-seq.html.
Unknown, "Geneious," Geneious Biologics, 2018, pp. 1-9, Retrieved from: https://www.geneious.com/.
Unknown, "Multiplex PCR. Premier Biosoft: Accelerating Research in Life Sciences," Premier Biosoft, 2018, pp. 1-4, retrieved from: http://www.premierbiosoft.com/tech_notes/multiplex-pcr.html.
Unknown, "Nucleotide Blast: Search Nucleotide Databases Using a Nucleotide Query," National Center for Biotechnology Information, U.S. National Library of Medicine, retrieved on Aug. 2021, pp. 1-5, retrieved from: blast.ncbi.nlm.nih.gov/Blast.cgi?PAGE_TYPE=BlastSearch.
Unknown, "P Values, False Discovery Rate and q-values," Nonlinear Dynamics: A Walters Company, 2018, pp. 1-4, Retrieved from http://www.nonlinear.com/support/progenesis/comet/faq/v2.0/pq-values.aspx.
Unknown, "SmartSEC® HT EV Isolation System for Serum & Plasma," SBI—System Biosciences, 2019, Version 1, pp. 1-12, System Biosciences (SBI), Palo Alto, California.
Unknown, "Sofosbuvir (Solvaldi)," Hepatitis C Online, 2018, pp. 1-3, Retrieved from https://www.hepatitisc.uw.edu/page/treatment/drugs/sofosbuvir-drug.
Untergrasser et al., "Primer3—new capabilities and interfaces," Nucleic Acids Research, 2012, vol. 40(15), pp. 1-12, Oxford University Press, Oxford, United Kingdom.
Vilar-Gomez et al., "Cost Effectiveness of Different Strategies for Detecting Cirrhosis in Patients With Non-alcoholic Fatty Liver Disease Based on United States Health Care System," Clinical Gastroenterology and Hepatology, 2020, vol. 18(1), pp. P2305-P2314.E12.
Wang et al., "RNA-Seq: a revolutionary tool for transcriptomics," Nature Genetics Review, 2009, vol. 10(1), pp. 57-63, Springer Nature Limited, Berlin, Germany.
Wilhelm-Benartzi et al., "Review of processing and analysis methods for DNA methylation array data," British Journal of Cancer, 2013, vol. 109, pp. 1394-1402, Nature Research, Berlin, Germany.
Xia et al., "NF-xB, and active player in human cancers," Cancer Immunology Research, 2014, vol. 2(9), pp. 823-830, American Association for Cancer Research, Philadelphia, Pennsylvania.
Younossi et al., "The Economic and Clinical Burden of Nonalcoholic Fatty Liver Disease in the United States and Europe," Hepatology, 2016, vol. 64(5), pp. 1577-1586, American Association for the Study of Liver Diseases, Alexandria, Virginia.
Zemel et al., "The Role of Oncogenic Viruses in the Pathogenesis of Hepatocellular Carcinoma," Clinics in Liver Disease, 2011, vol. 15(2), pp. 261-279, Elsevier, Amsterdam, Netherlands.
Zeringer et al., "Strategies for Isolation of Exosomes," Cold Spring Harbor Protocols, 2015, pp. 319-323, Cold Spring Harbor Laboratory Press, Cold Spring Harbor, New York.
Zhang et al., "IDH1/2 mutations target a key hallmark of cancer by deregulating cellular metabolism in glioma," Neuro-Oncology, 2013, vol. 15(9), pp. 1114-1126, Oxford University Press, Oxford, United Kingdom.
Zhang et al., "Liquid Biopsy for Cancer: Circulating Tumor Cells, Circulating Free DNA or Exosomes?" Cellular Physiology and Biochemistry, 2017, vol. 41, pp. 755-768, Karger, Basel, Switzerland.
Zheng et al., "Viral Oncogenes, Noncoding RNAs, and RNA Splicing in Human Tumor Viruses," International Journal of Biological Sciences, 2010, vol. 6(7), pp. 730-755, Ivyspring International Publisher, Sydney, Australia.
Ziller et al., "Coverage recommendations for methylation analysis by whole genome bisulfite sequencing," Nature Methods, 2015, vol. 12(3), pp. 230-232, Nature Portfolio, Berlin, Germany.
Akagi et al., "Genome-wide analysis of HPV integration in human cancers reveals recurrent, focal genomic Instability," Genome Research, 2014, 24(2), pp. 185-199, Cold Spring Harbor Laboratory Press, Cold Spring Harbor, New York.
Ammerpohl et al., "Distinct DNA methylation patterns in cirrhotic liver and hepatocellular carcinoma," International Journal of Cancer, 2012, vol. 130, pp. 1319-1328, UICC Global Cancer Control, Geneva, Switzerland.
Arulanandan et al., "Non-invasive Testing for Nash and Nash with Advanced Fibrosis: Are We There Yet?," Current Hepatology Reports, 2015, vol. 14(2), pp. 109-118, Springer, Berlin, Germany.
Aryee et al., "Minfi: a flexible and comprehensive Bioconductor package for the analysis of Infinium DNA methylation microarrays," Bioinformatics, 2014, vol. 30(10), pp. 1363-1369, Oxford University Press, Oxford, United Kingdom.
Bao et al., "Fluorescent Probes for Live-Cell RNA Detection," Annual Review of Biomedical Engineering, 2009, vol. 11, pp. 25-47, Annual Reviews, Palo Alto, California.
Bell, "CD4+ T Cells," Bitesize Immunology, British Society for Immunology, Retrieved on Aug. 24, 2021, Retrieved from, https://www.immunology.org/public-information/bitesized-immunology/cells/cd4-t-cells.
Bialecki et al., "Diagnosis of hepatocellular carcinoma," HPB☐: The Official Journal of the International Hepato Pancreato Biliary Association, 2005, vol. 7, pp. 26-34, Taylor & Francis Group, Milton Park, Oxfordshire.
Braicu et al., "Exosomes as divine messengers: are they the Hermes of modern molecular oncology?" Cell death and differentiation, 2015, vol. 22(1), pp. 34-45, Macmillian Publishers Limited, New York, New York.
Cavalcante et al., "Integrating DNA Methylation and Hydroxymethylartion Data with the Mint Pipeline," Cancer Research, 2017, vol. 77(21), pp. e27-e30, American Association for Cancer Research, Philadelphia, Pennsylvania.
Chalhoub et al., "PTEN and the PI3-Kinase Pathway in Cancer," Annual review of pathology, 2009, vol. 4, pp. 1-30, Annual Reviews, Palo Alto, California.
Cheng et al., "Integrative analysis of DNA methylation and gene expression reveals hepatocellular carcinoma-specific diagnostic biomarkers," Genome Medicine, 2018, vol. 10(42, pp. 1-11, BioMed Central Ltd, London, United Kingdom.
Clark et al., "Single-cell epigenomics: powerful new methods for understanding gene regulation and cell identity," Genome Biology, 2016, vol. 17(72), pp. 1-10, BioMed Central, London, United Kingdom.
De Oliveria Andrade et al., "Association Between Hepatitis C and Hepatocellular Carcinoma," Journal of global Infectious diseases, 2009, vol. 1(1), pp. 33-37, Wolters Kluwer, Philadelphia, Pennsylvania.
Drescher et al., "Current Status in Testing for Nonalcoholic Fatty Liver Disease (NAFLD) and Nonalcoholic Steatohepatitis (NASH)," Cells, 2019, vol. 8(845), pp. 1-23, MDPI, Basel, Switzerland.
Edgar et al., "Gene Expression Omnibus: NCBI gene expression and hybridization array data repository," Nucleic Acids Research, 2002, vol. 30(1), pp. 207-210, Oxford University Press, Oxford, United Kingdom.
Eissmann, "Natural Killer Cells," BiteSized Immunology, British Society for Immunology, Retrieved on Aug. 24, 2021, Retrieved from: https://www.immunology.org/public-information/bitesized-immunology/cells/natural-killer-cells.

(56) References Cited

OTHER PUBLICATIONS

Frenzel et al., "Bcl2 family proteins in carcinogenesis and the treatment of cancer," Apoptosis, 2009, vol. 14(4), pp. 584-596, Springer Nature, Switzerland.

Han et al., "The Epigenetic Regulation of HCC Metastasis," International Journal of Molecular Sciences, 2018, vol. 19, pp. 1-17, MDPI, Basel, Switzerland.

Hanahan et al., "Hallmarks of Cancer: The Next Generation," Cell, 2011, vol. 144, pp. 646-674, Elsevier, Amsterdam, Netherlands.

Hao et al., "DNA methylation markers for diagnosis and prognosis of common cancers," PNAS, 2017, vol. 114(28), pp. 7414-7419.

Haque et al., "A practical guide to single-cell RNA-sequencing for biomedical research and clinical applications," Genome Medicine, 2017, vol. 9(75), pp. 1-12, BioMed Central, London, United Kingdom.

Heimbach et al., "AASLD Guidelines for the Treatment of Hepatocellular Carcinoma," Hepatology, 2018, vol. 67(1), pp. 358-380, Wiley, Hoboken, New Jersey.

Hlady et al., "Initiation of aberrant DNA methylation patterns and heterogeneity in precancerous lesions of human hepatocellular cancer," Epigenetics, 2017, vol. 12(3), pp. 215-225, Taylor & Francis Group, Milton Park, Oxfordshire.

Hlady, et al., "Integrating the Epigenome to Identify Novel Drivers of Hepatocellular Carcinoma," Hepatology, 2019, vol. 69(2), pp. 639-652, Wiley, Hoboken, New Jersey.

Hughes et al., "The use of Multiple Displacement Amplified DNA as a control for Methylation Specific PCR, Pyrosequencing, Bisulfite Sequencing and Methylation-Sensitive Restriction Enzyme PCR," MNC Molecular Biology, 2007, vol. 8(91), pp. 1-7, BioMed Central, London, United Kingdom.

Hiwang et al., "Single-cell RNA sequencing technologies and bioinformatics pipelines," Experimental and Molecular Medicine, 2018, vol. 50(8), pp. 1-14, Nature Portfolio, London, United Kingdom.

Jaffe et al., "Bump hunting to identify differentially methylated regions in epigenetic epidemiology studies," International Journal of Epidemiology, 2012, vol. 41, pp. 200-209, Oxford University Press, Oxford, United Kingdom.

Jang et al, "Cancel cell metabolism: implications for therapeutic targets," Experimental & Molecular Medicine, 2013, vol. 45 (e45), pp. 1-8, Nature Portfolio, Berlin, Germany.

Jeong et al., "Hepatitis C virus and hepatocarcinogenesis," Clinical and Molecular Hepatology, 2012, vol. 18, pp. 347-356, Korean Association for the Study of the Liver, Seoul, Korea.

Jordan, "Epigenetics, DNA Methylation, and Their Role in Cancer," Microreviews in Cell and Molecular Biology, 2012, vol. 1(1), pp. 184-185, Oklahoma State University, Oklahoma.

Koressaar et al., "Enhancements and modification of primer design program Primer3," Bioinformatics Applications Note, 2007, vol. 23(10), pp. 1289-1291, The Authors, Oxford Academics, Oxford, United Kingdom.

Kutok et al., "Spectrum of Epstein-Barr Virus-Associated Diseases," Annual Review of Pathology: Mechanisms of Disease, 2006, vol. 1, pp. 375-404, Annual Reviews, Palo Alto, California.

Lau et al., "The Cancer Genomics Cloud: Collaborative, Reproducible, and Democratized—A New Paradigm in Large-Scale Computational Research," Cancer Research, 2017, vol. 77(21), pp. e3-e6, American Association for Cancer Research, Philadelphia, Pennsylvania.

Lee et al., "Epigenetic control of metastasis-associated protein 1 gene expression by hepatitis B virus X protein during hepatocarcinogenesis," Oncogenesis, 2012, vol. 1 (e25), pp. 1-9, Macmillan Publishers Limited, New York, New York.

Lehmann-Werman et al., "Identification of tissue-specific cell death using methylation patterns of circulating DNA," PNAS, 2016, pp. E1826-E1834.

Liaw et al., "Classification and Regression by randomForest," R News, 2002, vol. 2(3), pp. 18-22, The R Foundation, Vienna, Austria.

Liew et al., "The peripheral blood transcriptome dynamically reflects system wide biology: a potential diagnostic tool," Journal of Laboratory and Clinical Medicine, 2006, vol. 147(3), pp. 126-132, Science Direct, Amsterdam, Netherlands.

Lokk et al., "DNA methylome profiling of human tissues identifies global and tissue-specific methylation patterns," Genome Biology, 2015, vol. 15(r54), pp. 1-14, BioMed Central Ltd, Basel, Switzerland.

Macaulay et al., "G&T-seq: parallel sequencing of single-cell genomes and transcriptomes," Nature Methods, 2015, vol. 12(6), pp. 519-524, Nature Portfolio, Berlin, Germany.

Mesri et al., "Human Viral Oncogenesis: A Cancer Hallmarks Analysis," Cell Host & Microbe, 2014, vol. 15, pp. 266-282, Elsevier, Amsterdam, Netherlands.

Nishida et al., "Angiogenesis in cancer," Vascular Health and Risk Management, 2006, vol. 2(3), pp. 213-219, Dove Medical Press Limited, Macclesfield, United Kingdom.

Peng et al., "Child-Pugh Versus MELD Score for the Assessment of Prognosis in Liver Cirrhosis," Medicine, 2016, vol. 95(8), pp. 1-29, Lippincott, Williams & Wilkins, Philadelphia, Pennsylvania.

Pertea et al., "Transcript-level expression analysis of RNA-seq experiments with HISAT, StringTie, and Ballgown," Nature Protocols, 2016, vol. 11(9), pp. 1650-1667, Springer Nature Limited, Berlin, Germany.

Piazzolla et al., "Noninvasive Diagnosis of NAFLD and NASH," Cells, 2020, vol. 9(1005), pp. 1-17, MDPI, Basel, Switzerland.

Picelli et al., "Full-Length RNA-seq from single cells using Smart-seq2," Nature Protocols, 2014, vol. 9(1), pp. 171-181, Nature Publishing Group, Berlin, Germany.

Qi et al., "Circulating microRNAs (cmiRNAs) as novel potential biomarkers for hepatocellular carcinoma," Neoplasma, 2013, vol. 60(2), pp. 135-142, Journal of Experimental and Clinical Oncology, Bratislava, Slovak republic.

Risha, "The proteomic analysis of exosomes from breast cell lines reveals potential biomarkers of breast cancer," Thesis M.Sc. degree in Chemistry, 2020, pp. 1-91, University of Ottawa, Ottawa, Canada.

Sestakova et al., "DNA Methylation Validation Methods: a Coherent Review with Practical Comparison," Biological Procedures Online, 2019, vol. 21(19), pp. 1-11, BioMed Central Ltd, London, United Kingdom.

Snyder et al., "Cell-free DNA Comprises an In Vivo Nucleosome Footprint that Informs its Tissues-of-Origin," Cell, 2016, vol. 164, pp. 57-68, Elsevier Inc., Amsterdam, Netherlands.

Song et al., "Changed of guidelines diagnosing hepatocellular carcinoma during the last ten-year period," Clinical and Molecular Hepatology, 2012, vol. 18, pp. 258-267, The Korean Association for the Study of the Liver, Seoul, Korea.

Chen et al., "Analysis of DNA methylation and gene expression in radiation-resistant head and neck tumors," Epigenetics, Jun. 2015, vol. 10(6), pp. 545-561.

International Search Report and Written Opinion mailed Jan. 27, 2020 for International Patent Application No. PCT/US2019/040695.

Landi et al., "MicroRNA Expression Differentiates Histology and Predicts Survival of Lung Cancer," Clinical Cancer Research, Jan. 12, 2020, vol. 16(2), pp. 1-23.

Miura et al., "Amplification-free whole-genome bisulfite sequencing by post-bisulfite adaptor tagging," Nucleic Acids Research, May 30, 2012, vol. 40(17), pp. 1-9.

Wang et al., "Bead mediated separation of microparticles in droplets," PLoS One, Mar. 10, 2017, vol. 12(3), pp. 1-13.

Yang et al., "Exosomes mediate hepatitis B virus (HBV) transmission and NK-cell dysfunction," Cellular & Molecular Immunology, May 30, 2016, vol. 14(5), pp. 465-475.

Zubaite et al., "Droplet Microfluidics Approach for Single-DNA Molecule Amplification and Condensation into DNA-Magnesium-Pyrophosphate Particles," Micromachines, Feb. 27, 2017, vol. 8(2), pp. 1-13.

International Preliminary Report on Patentability dated Jan. 14, 2021, issued in International Application No. PCT/US2019/040695.

Bakker et al., Presentation and early detection of post-transplant lymphoproliferative disorder after solid organ transplantation. Transpl Int. 20(3):207-218 (2007).

(56) References Cited

OTHER PUBLICATIONS

Bodelon et al., Abstract 5580: Characterization of HPV integration sites in the human genome. Cancer Res. 75(15_Supplement):5580, 4 Pages (2015).

Chen et al., Analysis of DNA methylation and gene expression in radiation-resistant head and neck tumors. Epigenetics. 10(6):545-561 (2015).

Erdrich et al., Surgical and molecular characterization of primary and metastatic disease in a neuroendocrine tumor arising in a tailgut cyst. Cold Spring Harb Mol Case Stud. 4(5):a003004, pp. 1-12 (2018).

Landi et al., MicroRNA expression differentiates histology and predicts survival of lung cancer. Clin Cancer Res. 16(2):430-441 (2010).

Llovet et al., Sorafenib in advanced hepatocellular carcinoma. N Engl J Med. 359(4):378-390.(2008).

Miura et al., Amplification-free whole-genome bisulfite sequencing by post-bisulfite adaptor tagging. Nucleic Acids Res. 40(17):e136, pp. 1-9 (2012).

Snyder, et al. Cell-free DNA comprises an in vivo nucleosome footprint that informs its tissues-of-origin. Cell 164(1-2):57-68 (2016).

Sun et al., High-resolution enzymatic mapping of genomic 5-hydroxymethylcytosine in mouse embryonic stem cells. Cell Reports. 3(2):567-576 (2013).

Ting et al., Endogenous retroviral sequences are required for tissue-specific expression of a human salivary amylase gene. Genes Dev. 6(8):1457-1465 (1992).

Unknown, Burkitt Lymphoma. Lymphoma Research Foundation (Web Archive Jan. 15, 2018). Retrieved from https://web.archive.org/web/20161015145056/http://www.lymphoma.org/site/pp.asp?c=bkLTKaOQLmK8E&b=9445353.

Unknown, Cervical Cancer: Screenings. US Preventative Services and Task Force, 1 page (Web archive Jul. 18, 2015). Retrieved from https://web.archive.org/web/20150718042249/http://www.uspreventiveservicestaskforce.org/Page/Document/UpdateSummaryFinal/cervical-cancer-screening.

Wang et al., Bead mediated separation of microparticles in droplets. PLoS One. 12(3):e0173479, pp. 1-13 (2017).

Yang et al., Exosomes mediate hepatitis B virus (HBV) transmission and NK-cell dysfunction. Cell Mol Immunol. 14(5):465-475 (2017).

Ziller et al. Coverage Recommendations for Methylation Analysis by Whole-Genome Bisulfite Sequencing. Nature Methods 12(3):230-232 (2015).

Zubaite et al., Droplet microfluidics approach for single-DNA molecule amplification and condensation into dna-magnesium-pyrophosphate particles. Micromachines. 8(2):62, pp. 1-13 (2017).

\* cited by examiner

SEQUENCE LISTING

```
<160> NUMBER OF SEQ ID NOS: 277

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
cgactacatc aaaggcagca a                                                 21

<210> SEQ ID NO 2
<211> LENGTH: 21
<212> TYPE: DNA
<213> ORGANISM: Artificial Sequence
<220> FEATURE:
```

<223> OTHER INFORMATION: Description of Artificial Sequence: Synthetic
       probe

<400> SEQUENCE: 2
ccaccagaag aagagaagaa t                                              21

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 3
ccgagcgatt tcaaatttcc ct                                             22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 4
cgagatggaa ttaacagtct t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 5
cagtgactaa ttgtgagtct t                                              21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 6
actatggcaa catcagccg                                                 19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 7
gaaacagctg ccttagcttc a                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 8
gcacaagttt gcctacaatg                                                   20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gcggcagacg tatgatgaca t                                                 21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
tcgcagagaa atcgggcatt t                                                 21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11 tcagggcct ggctggttca                                                    20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
cggcggtagc ttatcagact ga                                                22

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gagctagcac ttcccgagc                                                    19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
cctcggatgg gaattggata                                                     20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tcctgtcaca aatcacattg c                                                   21

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
gtaaacatcc tcgactggaa gct                                                 23

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
acccaactca cttctgcctt                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gcttctttac agtgctgcct                                                     20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
cttaggtggg actcgcctc                                                      19

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 20
cagtggtttt accctatggt agg                                          23

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tgtagtgttt cctactttat ggatgtagtg tttcctactt tatgga                 46

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gaggaagaca gcacgtttgg t                                            21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ttctgcaaat caaatcatta gc                                           22

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tcaaagacat tttctcagac attca                                        25

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 25
uaugcaaggg caagcucucu uc                                           22

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
```
cgccttctct tcccggt                                          17

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ctgactccta gtccagggct                                       20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
agtgccttat tcaggaaggt gt                                    22

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gatccaagac tggctgactt c                                     21

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
caccggatgg acagaca                                          17

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tggcttaatc tcagctggca                                       20

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32

```
tgccccatga acagtctcca ccac                                          24
```

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33

```
tgtcaacaac cgaccttgat t                                             21
```

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34

```
gctgctcggg tgtgctgcct t                                             21
```

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35

```
ctgcagatga gtgtgccaac                                               20
```

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36

```
gctgtttctg gggattaaat aagac                                         25
```

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37

```
ctgatgacca gcaacttgat t                                             21
```

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38

```
atggcgatga gcccaggtcc tttgttc                                       27
```

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
agttcccgga gtgagttgaa                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
acggctcaat gtttggagac                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
ccacaagaca gaagctgaag                                              20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
gaccgaagag tttgtagaga a                                            21

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
atccgcagac gtgtaaatgt tcct                                         24

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
tgacgtcact ggagttgtac gg                                           22

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
gcctgctgaa aatgactgaa tataaac                                          27

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
cccgctacgt aatcagtcgg                                                  20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
atgacggaat ataagctggt g                                                21

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
acgacggtga cacgcttccc tg                                               22

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
gcgggcacag acgcccagga ccgagct                                          27

<210> SEQ ID NO 50
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
agctctagat gccatccgtg cctctgagat cccatttcac gctgaaggcc                 50

```
<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
gcgggataca atatttagct t                                              21

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
caagactgct agccgagtag tgttgggtcg                                     30

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
caggactgtg aaagccatca cggg                                           24

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
gccatgatct actgctctca t                                              21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
gctccagaag ttgcttgtgc                                                20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
gctgcagtgg gaccactatt                                                20

<210> SEQ ID NO 57
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
agcttatgtc aggggctttg                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
ctggggcttt gtggtacgag                                                   20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
gagcccctgg tgctccatga g                                                 21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
gctctccatc ctatgttgcg g                                                 21

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
ctgagagagg caggcgatg                                                    19

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
gcgatcatga atttcaagaa a                                                 21

<210> SEQ ID NO 63
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(21)
<223> OTHER INFORMATION: Description of Combined DNA/RNA Molecule:
      Synthetic probe

<400> SEQUENCE: 63
cuacgugacu cauccgaaat t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
cccttccttc aatagcacta t                                              21

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
tgatgtgata aaccgtggtg                                                20

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
cgataccttc actcgaaact t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
gatgagtaac tggcttcctt t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 68
catcgagtca tcttgggcaa t                                              21
```

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
gctggagaat tacacaccca a                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
acatcgaccc gtccacagta t                                              21

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
ctgtggtctg gtgctggtc                                                 19

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
agaaacctca agatgtggat t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
gaaagagatg caaaggatcc t                                              21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
aggaactgtg tacgccattt a                                              21

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75 cttttcttg ccctcactgc                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
ggtccatgtc cgcgtcccac                                             20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
gattcaggaa cacatttatg                                             20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
gatgacctgc caacagacca                                             20

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
catgcgaact gccatctg                                               18

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
tgccagcaac actaccacag                                             20

-continued

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
aggaaggaga ttgggtgaat c                                             21

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
agagcgaccc tcacatcaag                                               20

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
ccagggacct ctctctaatc agc                                           23

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
ccatcgtgat tgggatcact a                                             21

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
cgctcatagt tcgttacacc                                               20

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
gaccaatgca taaggcatta t                                             21

<210> SEQ ID NO 87

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
cgtgtgcttc gttcaatcct a                                              21

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
ggctgggaaa tgatgagaag at                                             22

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
gtgcctatga tgaagcgttt a                                              21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
gagcgataag ttcacacggt t                                              21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
gcagaactgt atcaaggaag t                                              21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
ccacaggaag atatggacca t                                              21

<210> SEQ ID NO 93
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
caggcctaca ggttccaaga                                              20

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
catcaccaag ctcaagtatt a                                            21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
ctagttgcta agctcgacct a                                            21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
ctgagaggac catggactta g                                            21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
cgacctggag aacatcatct t                                            21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
gaagaaattc accgatgacc t                                            21

<210> SEQ ID NO 99
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 99
cctttgatgg tcgagacata a                                           21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 100
cgggaagatt attagttggt a                                           21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
cctgggttgg aagtcgatgt t                                           21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
cctgccaaga gaacagacta t                                           21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
gctaacatta ggagcctata a                                           21

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
tgaggagaat atccatta                                               18

<210> SEQ ID NO 105
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 105
cggtggtacg tctactgtaa a                                              21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
gttatgggta agaaggcatt a                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
gcagacttac aatggcaatg a                                              21

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
gtgtggctga cgtagttgta tgta                                           24

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
cctcctttct atctgctcac t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
ccaccctcaa agtgaggatt a                                              21

<210> SEQ ID NO 111
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 111
gtacaataac ttgcctgaaa t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
cctacagtta cgtgtgtgga a                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
gcaagcagac cttcgcatca a                                              21

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
taccaccagg accagtcatc                                                20

<210> SEQ ID NO 115
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
acggccttca acaccagaa                                                 19

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
caagctctat ggctcgccct t                                              21

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued

```
      probe

<400> SEQUENCE: 117
ctatcttgtg tacttcca                                                 18

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 118
cagatgaacg tatttcctgt t                                             21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
ctacactctc ttcaatctaa t                                             21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
cgccattcct attgaaatca t                                             21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
tggggtaaag ggaatcaaaa g                                             21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
gtggtctctc tggttgtgta t                                             21

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 123
gtcatttcat ttcttttct tttct                              25

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 124
cctgagctct atctcagtgt a                                 21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
gtgctggatg aacgcctggt t                                 21

<210> SEQ ID NO 126
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 126
ggccaagccc tggtatgag                                    19

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 127
agttcttact caaatgggtt ca                                22

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
attcccaact tcttctggag                                   20

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 129
gactttgttg taatagatcc c                                          21

<210> SEQ ID NO 130
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 130
catcctgaag caaaagattt aatgac                                     26

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
cccaccacgt acaagggtc                                             19

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 132
aagatgctgg ctgagctgta cg                                         22

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 133
ttcttgcagc caccctgc                                              18

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 134
aatccagaac acaaccttgt c                                          21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 135
```
gatggtgtca aggaagtgtt c                                             21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 136
gtcagaacac tccacaggta t                                             21

<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
ccacctgggc cagtattat                                                19

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 138
gcgtgtcttc acagatctga a                                             21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 139
ccaggctgga aatggaacat t                                             21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140
cacacagaac tggagaaata t                                             21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 141
ttgctgcctt tgatgtagtc g                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 142
attcttctct tcttctggtg g                                              21

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143
gagtgggtgg ggagggg                                                   17

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 144
aagactgtta attccatctc g                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 145
aagactcaca attagtcact g                                              21

<210> SEQ ID NO 146
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
agctcatccc cagtccg                                                   17

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
tgaagctaag gcagctgttt c                                              21

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
ttctggacta cacggtttgg                                              20

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
atgtcatcat acgtctgccg c                                            21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
aaatgcccga tttctctgcg a                                            21

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 151
gttcaccgct cgcctccacc                                              20

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
ctggtgtcgt ggagtcggca attc                                         24

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
tagctgtctg ccccttgtct                                              20

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
agaggcgcac aggaagga                                                 18

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
agagttgggg atcagggc                                                 18

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
gctgcaaaca tccgactgaa                                               20

<210> SEQ ID NO 157
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 157
ttcctctata agcatactgt ttttctg                                       27

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
ttcatagccc tgtacaatgc t                                             21

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
acccagagtg ctaggggttt                                               20

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 160
cgtggttcta ccctgtggta g                                              21

<210> SEQ ID NO 161
<211> LENGTH: 16
<212> TYPE: DNA
<213> ORGANISM: Artificial Sequence
<220> FEATURE:
<223> OTHER INFORMATION: Description of Artificial Sequence: Synthetic probe

<400> SEQUENCE: 161
aaaggcgcag cgacgt                                                    16

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 162
ttcttcctcc ataaaatggg g                                              21

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 163
gattgcagga ccatttctgg                                                20

<210> SEQ ID NO 164
<211> LENGTH: 17
<212> TYPE: DNA
<213> ORGANISM: Artificial Sequence
<220> FEATURE:
<223> OTHER INFORMATION: Description of Artificial Sequence: Synthetic probe

<400> SEQUENCE: 164
ttcgccctct caaccca                                                   17

<210> SEQ ID NO 165
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 165
ctccagaccc ctcgttca                                                  18

<210> SEQ ID NO 166

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
ccaccacaaa tgttgtccat gt                                           22

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
gtgctctatt accggggttt                                              20

<210> SEQ ID NO 168
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
cggtccagct ctccagt                                                 17

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
tgagggctag gaaattgctc t                                            21

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
ccccataggc ctaccccatt acca                                         24

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
tcaaggtcgg ttgttgacat t                                            21

<210> SEQ ID NO 172
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 172
ggcagcacac ccgagcagct t                                            21

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
ccagtagcat cgttttcttg act                                          23

<210> SEQ ID NO 174
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 174
ccgcagggaa tatctggct                                               19

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 175
tcaagttgct ggtcatcagt t                                            21

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
ctatggactg ataaaagact catcaaa                                      27

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 177
ctccactcct ccctttcctc                                              20

<210> SEQ ID NO 178
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 178
tggagtgaac accaaaacca                                                    20

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
agatactatc tgtaagtgaa cc                                                 22

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 180
ttctctacaa actcttcggt c                                                  21

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
tcaccgcctt ggcttgtcac                                                    20

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 182
ggttcatgtc atggatggtg c                                                  21

<210> SEQ ID NO 183
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 183
tgattctgaa ttagctgtat cgtcaag                                            27

<210> SEQ ID NO 184
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 184
catgactcgt ggttcggagg                                              20

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
ggagagcaca cacttgcagc tcat                                         24

<210> SEQ ID NO 186
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 186
cgctaggatc tgactgcggc tc                                           22

<210> SEQ ID NO 187
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 187
gcggaaagga aggggagggg ctggga                                       26

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
gctaaatatt gtatcccgct t                                            21

<210> SEQ ID NO 189
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 189
tcgggcacga gacavgctgt gatatatg                                     28

<210> SEQ ID NO 190
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 190
ctggaaaatc tgcctccccg tgat                                          24

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
atgagagcag tagatcatgg c                                             21

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 192
aaccagaggg ctgttgatgg                                               20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 193
tgtggccttg tactgcagag                                               20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 194
agagagcgtg ccaataactc                                               20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 195
ggccattgac agagacgaca                                               20

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued

```
       probe

<400> SEQUENCE: 196
aggactctga cactgtccaa cttg                                          24

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
tccaagtaac tcggtcatca tct                                           23

<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 198
cgatgcgacc ccagtttac                                                19

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 199
tttcttgaaa ttcatgatcg c                                             21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (1)..(21)
<223> OTHER INFORMATION: Description of Combined DNA/RNA Molecule:
      Synthetic probe

<400> SEQUENCE: 200
uuucggauga gucacguaga t                                             21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 201
atagtgctat tgaaggaagg g                                             21

<210> SEQ ID NO 202
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 202
tggatcgggc aaggaaa                                                  17

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 203
aagtttcgag tgaaggtatc g                                             21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 204
aaaggaagcc agttactcat c                                             21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 205
attgcccaag atgactcgat g                                             21

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 206
tgggtgtgta attctccagc                                               20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 207
cagaggggta ggcttgtctc                                               20

<210> SEQ ID NO 208
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 208
tgggcaactt gaagagtgtg                                                20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
atccacatct tgaggtttct                                                20

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 210
aggatccttt gcatctcttt c                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 211
taaatggcgt acacagttcc t                                              21

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
acagcagcca gattcctcat                                                20

<210> SEQ ID NO 213
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 213
aatgacatct aggtctccgg ccctg                                          25

<210> SEQ ID NO 214
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 214
cataaatgtg ttcctgaatc t                                              21

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
ccccaggatt tcttgccctt                                                20

<210> SEQ ID NO 216
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 216
tatgcctctc gagctggg                                                  18

<210> SEQ ID NO 217
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 217
gtgattattc cacatgtaat tggtg                                          25

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 218
gcaccaaggg gaaaaatta                                                 19

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
actgcccagt tcgtttcagt                                                20

<210> SEQ ID NO 220
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 220
ctcagcttga gggtttgcta caa                                              23

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221
tagtgatccc aatcacgatg g                                                21

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
ccagggacag atagtcttca                                                  20

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
ataatgcctt atgcattggt c                                                21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
taggattgaa cgaagcacac g                                                21

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
cacagttgcc ttcaaactta tc                                               22

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 226
taaacgcttc atcataggca c                                          21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
aaccgtgtga acttatcgct c                                          21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
acttccttga tacagttctg c                                          21

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
tggtccatat cttcctgtgg                                            20

<210> SEQ ID NO 230
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
ctggaaagat ggaggcagc                                             19

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
taatacttga gcttggtgat g                                          21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      probe -continued

<400> SEQUENCE: 232
taggtcgagc ttagcaacta g                                    21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
ctaagtccat ggtcctctca g                                    21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
aagatgatgt tctccaggtc g                                    21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
aggtcatcgg tgaatttctt c                                    21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
ttatgtctcg accatcaaag g                                    21

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 237
accaactaat aatcttcccg                                      20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 238
acatcgactt ccaacccagg                                                    20

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239
atagtctgtt ctcttggcag g                                                  21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
ttataggctc ctaatgttag c                                                  21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241
taataatgga tattctcctc a                                                  21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242
tttacagtag acgtaccacc g                                                  21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 243
taatgccttc ttacccataa c                                                  21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244
```
tcattgccat tgtaagtctg c                                             21

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245
gtagatgagc cctgagtagt aacg                                          24

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
agtgagcaga tagaaaggag g                                             21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247
taatcctcac tttgagggtg g                                             21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 248
atttcaggca agttattgta c                                             21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
ttccacacac gtaactgtag g                                             21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 250
ttgatgcgaa ggtctgcttg c                                              21

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 251
gccagacctc caaagttagc                                                20

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
cattctggtg ttgaaggccg t                                              21

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 253
agggcgagcc atagagcttg                                                20

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 254
tactggaagt acacaagata g                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255
aacaggaaat acgttcatct g                                              21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
attagattga agagagtgta g                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
atgatttcaa taggaatggc g                                                21

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
cctatgcaat cggtctttgc                                                  20

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
atacacaacc agagagacca c                                                21

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
ctgcacgctc tatactgcaa atg                                              23

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
tacactgaga tagagctcag g                                                21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
aaccaggcgt tcatccagca c                                                21

```
<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
tagtcgggcc gattgatctc                                              20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 264 aggctcctttt gtcagttctc                                             20

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
tggacacagt agagcctc                                                18

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
aagaacaaac ctaaacctaa a                                            21

<210> SEQ ID NO 267
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
tggtaattta gaattctgtc cctttattc                                    29

<210> SEQ ID NO 268
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
ctggggtatt gggggcatc                                               19
```

```
<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269
gatccaggtt gcaatgaggt tg                                              22

<210> SEQ ID NO 270
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
cttgcgtttc tcagtccga                                                  19

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271
caaggttgtg ttctggattc t                                               21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 272
gaacacttcc ttgacaccat c                                               21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
atacctgtgg agtgttctga c                                               21

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 274
ataatactgg cccaggtgg                                                  19

<210> SEQ ID NO 275
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
ttcagatctg tgaagacacg c                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 276
aatgttccat ttccagcctg g                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
atatttctcc agttctgtgt g                                              21
```

METHODS FOR DETECTING AND TREATING A TUMORIGENIC PHENOTYPE OF THE LIVER

CROSS-REFERENCE TO RELATED APPLICATIONS

This application is a U.S. national stage filing under 35 U.S.C. § 371 of International Application No. PCT/US2019/040695, filed Jul. 5, 2019, which claims priority to and the benefit of U.S. Provisional Application No. 62/694,325 filed Jul. 5, 2018, which is hereby incorporated by reference in its entirety.

All references cited herein, including but not limited to patents and patent applications, are incorporated by reference in their entirety.

REFERENCE TO SEQUENCE LISTING SUBMITTED ELECTRONICALLY

The content of the electronically submitted sequence listing in ASCII text file (Name: 1988-0010US01_Sequence_Listing_ST25.txt; Size: 62 KB; and Date of Creation: Jul. 26, 2021) filed with the application is incorporated herein by reference in its entirety.

BACKGROUND

Oncogenes of HBV (Hepatitis B Virus) and HCV (Hepatitis C Virus) cause hepatocellular carcinomas (HCC), and both viruses can lead to chronic infections of the liver (or hepatitis).[1] Persistent hepatocellular infections lead to reactive oxygen species (ROS) accumulation, which causes the first stage of liver scaring (fibrosis), and over time can lead to cirrhosis in which hepatocytes cannot carry out formal function. This ultimately causes hepatocellular carcinoma.[1] Although HBV and HCV both lead to HCC, their oncogenes and pathways vary.

HBV HCC is caused by HBV encoded X protein (or HBx protein) binding to and downregulating p53, leading to loss of its tumor suppression activity, phosphorylation of Rb proteins, and inactivation of various Cyclin-dependent kinase (Cdk) inhibitors.[2] These processes lead to replicative immortality from stimulation of human telomere reverse transcriptase (hTERT) overexpression (which is commonly seen in various other oncogene transductions).[1,2] HBx enables infected cells to evade apoptosis by blocking antiviral signaling proteins produced by the mitochondria. HBx also downregulates TGF-β and uses this pathway to promote immortalization and tumorigenesis.[1,2]

HCV infections can also cause HCC. HCC induced by HCV can be initiated by three viral oncogenes: HCV encoded core protein, nonstructural protein 5A (Ns5A), and nonstructural protein 3 (Ns3).[3] These oncogenes initiate common cancer hallmarks by downregulating various tumor suppressor proteins, such as p53, hTERT, Rb, and TGF-β (transforming growth factor beta).[1,2,3] These factors lead to liver cell proliferation and survival in a similar manner to Ns5A evading apoptotic pathways by blocking inhibiting caspase-8 in HBV infection. Ultimately, HCV promotes controlled growth, overexpresses telomerase and promotes cellular survival by escaping checkpoints.[1,2,3]

HCC is usually not detected until liver cirrhosis is evident. Thus, HCC patients have poor prognosis with an average survival of 6-20 months after initial diagnosis.[4] Furthermore, HCC infects close to 40,000 patients in 2016 in the US, causing more than 27,000 deaths. Incidence of HCC is currently on the rise to become one of the leading causes of cancers both in the US and worldwide.[5] Diagnostics for HCC include, serum tumor marker alfa-fetoprotein (AFP) (an elevated glycoprotein) in 20%-40% of HCC patients. However, many HCC patients have low levels of AFP even after diagnostics, and thus AFP is not an efficient diagnostic.[4] Furthermore, patients are often not screened asymptomatically further contributing to poor prognosis.

Cirrhosis precedes HCC, and symptoms of advanced cirrhosis include jaundice, hepatic encephalopathy, anasarca and upper right quadrant pain.[4] A comprehensive metabolic panel (CMP) or liver panel including testing for alanine aminotransferase (ATL), aspartate aminotransferase (AST), and alkaline phosphate (ALP) can be performed. These markers are often increased due to cirrhosis. Albumin protein, which is downregulated due to cirrhosis, can also be measured.[6] Testing for the presence of HBV and HCV antigens can be performed to help determine the underlying cause.[6] Once symptoms become evident, and are confirmed through testing, nodules that are less than 1 cm in diameter are screened through ultrasound or other imaging techniques, and assessed every 4 to 6 months to determine if the nodules have grown.[7] If tumor growth exceeds 2 cm, radiological testing is recommended. Such testing can include magnetic resonance imaging scan (MRI) specific for hepatocytes in conjunction with computerized tomography (CT) scans.[7]

Analyses for staging prognosis of HCC include Child-Pugh classification, albumin and bilirubin levels, prothrombin time (clotting time), hepatotoxicity in blood, and cirrhotic swelling.[8] Other common staging methods include determining the Model for End-Stage Liver Disease (MELD) score, and measuring bilirubin, prothrombin time and creatinine levels.[8]

Sofosbuvir (or Savaldi) can be used to inhibit Hepatitis C Virus (HCV) replication and has shown a 90% cure rate. However, treatment currently costs $84,000, thus many patients are unable to access this treatment.[9] Chemotherapy and radiation can be used as alternative treatments. Often, liver transplants are the most effective treatment to chronic hepatitis followed by HCC.[10] Although the role of hepatitis B and C in oncogenesis is known, the current available information is not yet predictive for risk assessment of developing cancer. What is needed is an early detection system and method to provide predictive information at an earlier stage of the disease than current methods.

SUMMARY

Aspects described herein bridge the gap between primary care physicians and genetic tools in order to diagnose patients at an early stage of their disease. Viral oncogene expression in patients can be tracked periodically by monitoring changes in RNA expression of viral oncogenes, somatic mutation and cancer hallmarks as indicators of the onset of tumorigenesis.

Patients can provide blood samples as part of a routine examination. The blood samples can be tested for RNA expression levels of viral oncogenes and the information can be provided to the patient and their doctor to facilitate early detection of tumorigenesis.

In another aspect, targeted RNA sequencing can be used to determine gene expression profiles of oncogenes. Aspects described herein will connect transcriptomics and primary care physicians. Yet further aspects utilize methods of analyzing viral oncogenesis and targeted transcriptomic sequencing technologies to improve cancer diagnosis.

In another aspect, methods for multiplexing probes to detect epigenetic heterogeneity in various tissues by determining transcriptional expression will facilitate a better understanding of disease progression in patients.

Methods and kits described herein analyze the source of tumor and progression of varying stages of hepatocellular carcinoma (HCC) through the analysis of differential expression of viral oncogenes, somatic mutations, cancer hallmarks, and methylation patterns.

One aspect provides methods of identifying at least one methylation pattern in a nucleic acid isolated from at least one exosome or circulating tumor cell in a blood sample by obtaining the blood sample from a patient; isolating the at least one exosome or circulating tumor cell from the blood sample; isolating the nucleic acid from the at least one exosome or circulating tumor cell; identifying a tissue source of the at least one exosome or circulating tumor cell; and identifying a methylation pattern corresponding to a degree of methylation of the nucleic acid. In another aspect, at least one transcription pattern of a nucleic acid is identified. In a further aspect, the at least one methylation pattern and at least one transcription pattern of a nucleic acid are indicative of a phenotype (e.g., pre-tumorigenic, tumorigenic, normal, etc.).

Further aspects provide a kit having at least a first probe for identifying a first methylation pattern in a nucleic acid isolated from an exosome or circulating tumor cell and at least a second probe for identifying a second methylation pattern in the nucleic acid, wherein the second methylation pattern comprises the degree of methylation of the nucleic acid, and a third probe for identifying transcriptional patterns of nucleic acid.

DETAILED DESCRIPTION

Figure 1A:
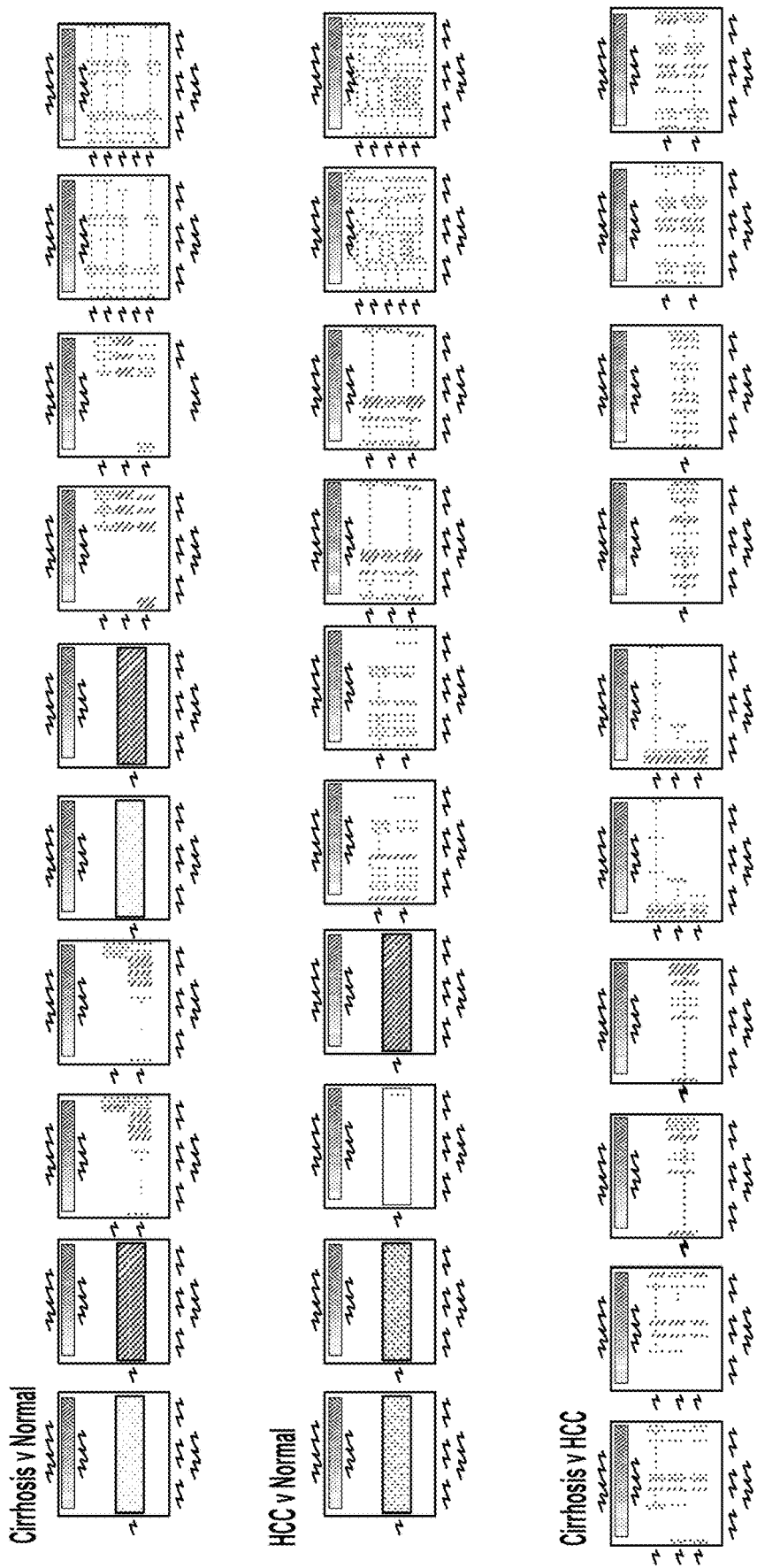
FIGS. 1a-1b provides exemplary Exon-Intron structure comparisons of RNA-Seq data of cirrhotic-normal, HCC-normal and cirrhotic-HCC sample comparisons and potential novel transcripts.

One of the major limitations to the current transcriptomics market is the absence of genetic technologies in primary care. The next stage of the genomics revolution can focus both on detection, as well as quantifying information obtained. There is a major demand for genomic sequencing services in primary care. Although RNA and DNA sequencing technologies have advanced rapidly in the last few decades, there is a desire for new services to offer patients medical analyses of transcription and genomic analysis for early diagnosis.

Methods, compositions, and kits are provided for targeted transcription sequencing of viral oncogenes to determine gene expression profiles for early diagnosis of cancer. As described herein, RNA-Sequencing and other techniques can be used to introduce transcriptomics techniques into modern medicine.

In one aspect, methods described herein could redefine staging of cancer to be seen through a new paradigm—precancerous stages that lead up to cancerous stages (and various other cancer stages) contributing to alterations in viral oncogene expression in conjunction with aberrant transcriptional expression changes.

Viral oncogene and aberrant transcriptional expression and their relation to disease prognosis can be analyzed by using cell free DNA (cfDNA).[12] cfDNA can be found in tissues, such as the bloodstream, urine, stool, saliva and various other tissues. cfDNA contains nucleosomes that show gene structure and contain biomarkers to reveals the cell or tissue of origin. Nucleosome footprints from cfDNA contain nucleic acid transcripts unique to specific cellular types (i.e. a distinct transcriptional expression for the liver, the cervix, etc). Circulating nucleosome footprints can indicate pathological states, including nucleosome footprints derived from tumor-derived exosomes or nucleosomes.

In this aspect, cfDNA can be used as a powerful tool to determine both the presence and tissue source of the cancer by measuring transcriptional markers. Exosome and cfDNA modified, for example, by cellular death or prolonged tissue damage associated with tumors are identifiable through protein-DNA alternations.[12]

Peripheral blood cells (or PBCs) are circulating blood cells that have been shown to express large portions of genes found in various tissues of the body including, the brain, colon, heart, kidneys, liver, lungs, spleen, prostate and stomach.[11] However, more than 80% of genes expressed in specified tissues are shown to also be expressed in PBCs. This indicates that PBCs and cfDNA could potentially be used as markers to correlate expression levels to diseases and cancers.[11]

Aspects described herein provide methods of identifying at least one methylation pattern in a nucleic acid isolated from at least one exosome or circulating tumor cell in a blood sample, by obtaining the blood sample from a patient; isolating the at least one exosome or circulating tumor cell from the blood sample; isolating the nucleic acid from the at least one exosome or circulating tumor cell; identifying a tissue source of the at least one exosome or circulating tumor cell; and identifying a methylation pattern corresponding to a degree of methylation of the nucleic acid.

In another aspect, cell surface antigens or another identifying feature can be used to identify the tissue source of an exosome or circulating tumor cell. In a further aspect, the methylation pattern can correspond to the degree of methylation of the nucleic acid, wherein the degree of methylation indicates a tumorigenic phenotype.

In a further aspect the degree of methylation of the nucleic acid is determined by measuring the level of methylation in the exosome or circulating tumor cell compared to a control cell. The term "control cell" refers to a cell that does not exhibit a tumorigenic phenotype. For example, with respect to a liver cell, a normal cell can include a non-tumorigenic normal cell and a non-tumorigenic cirrhotic cell.

The term "exosome" refers to extracellular vesicles of endosomal origin and produced by eukaryotic cells. Exosomes are extracellular vesicles less than 200 nm in diameter found in fluids such as blood or urine.[13] Exosomes are released from tumor cells and move to other cells for communication, they contain genetic information of DNA, RNA and proteins within the inner compartments, thus are desirable biomarker candidates.[13]

Exosome isolation can be performed through ultracentrifugation, precipitation polymers or affinity based capture.[14] Affinity based capture are effective methods that use purification of specific antibodies against various surface markers, such as but not limited to, MHC Class I and II molecules, EGFRvIII, LFA-3/CD58, EpCAM. Rab5, CD9, CD18, CD63, CD81, CD82, CD146, Alix or annexin.[14,15]

In one aspect, antibodies are immobilized through magnetic beads or microfluidic device that can capture and identify surface markers of interest from liquid biopsies (such as blood, serum, urine, ect). Vn peptides could also be used to capture exosomes through the Vn96 peptide. Protocols for antibodies against these surface markers have been developed for commercial use, such as New England Peptide or through Life Technologies for exosome capture.[14]

Methods of analyzing target cell surface markers that are present on the outside of exosomes in both healthy and diseased hepatocytes can be used in accordance with aspects described herein. In this aspect, the surface marker is not used as a biomarker for tumorigenesis, but as the first step to targeting hepatocyte cells to then investigate a multiplicity of cellular interactions, such as, but not limited to, oncogenes expression, overall transcriptional expression patterns and methylation patterns within the same cell that have statistical significance of two or more events occurring simultaneously in order to differentiate heathy state from HCC state.

The term "circulating tumor cell" (CTCs) refers to a tumor cell or pre-tumor cell that is released from a primary tumor into blood circulation. Tumor growth passively releases CTCs into the bloodstream, platelets facilitate epithelial-to-mesenchymal transition (EMT) by forming a protective barrier around CTCs to support adhesion to distal organs for invasion and metastasis.[16]

Detection of CTCs can use surface markers for identification. Epithelial cell markers can be used for positive selection, such as EpCAM (epithelial cell adhesion molecules) or cytokeratin markers (which are found in the cytoskeleton of epithelial tissue).[16] However, most CTCs lose their epithelial phenotypes, thus, either mesenchymal markers or a combination of mesenchymal and epithelial markers would need to be targeted for cellular selection.[16] Certain chip based microfluidics have been developed to enhance CTC capture, by performing microfluidic isolation prior to the labeling step, in which microfluidic antibodies-coated against surface markers capture specific cells.

The term "blood sample" refers to a volume of blood or fractionated blood, or a portion thereof obtained by a patient or subject. The blood sample may be drawn by a doctor, nurse, phlebotomist, or the patient or subject.

In further aspects, the degree of methylation of the nucleic acid can be determined by measuring the level of methylation in the exosome or circulating tumor cell compared to a control normal cell, and a chronic cirrhosis cell. For example, the degree of methylation can be determined using bisulfate-sequencing (e.g., post-bisulfate adapter-tagging (PBAT)).

In yet another aspect, a degree of methylation of at least a log change in the level of the nucleic acid with a change in β greater than 0.2 compared to the level of a control nucleic acid indicates a tumorigenic phenotype.

Conventional bulk population sequencing (such as whole genome or RNA sequencing) can only average expressional signals for an ensemble of cells. Single cell sequencing does not rely on bulk averages, but instead quantifies specific intracellular interactions.[17]

In some aspects, high throughput single cell sequencing can be run in parallel through RNA sequencing and genome sequencing for intricate analysis of heterogeneity in the same cell.[17] Single cell sequencing follows similar methods as conventional sequencing, such as isolation, lysis, reverse transcriptase of first and second strands, followed by amplifications.

Single cell sequencing is conducted by RNA-Seq, DNA-Seq, Bisulfite-Seq (BS-Seq), Reduced Representation Bisulfite Sequencing, Methyl-Seq, Massively-Paralleled RNA-Seq, Tet-associated Bisulfite (TAB)-seq, AbSI(Aba)-seq, and/or Chip-Seq.[18]

For single cell isolation, limiting methods such as flow activated cell sorting (FACS) relies on large starting volume and requires monoclonal antibodies. Microdroplet based microfluidics, are lower in cost and have seen recent advancements that allow for the monodispersion or encapsulation of thousands to millions of cells by running cells in an aqueous oil phase.[17] Droplet based protocols can eliminate the need for cell sorting through FACS, because these methods contain all necessary reagents for lysis, molecular tagging and reverse transcriptase.[20] Some droplet based protocols, such as 10× Genomics enable high throughput analysis of the 3' end of mRNA and have been approved for clinical and commercial use.[17]

Various sequencing protocols utilize bead integration during the first step of cDNA synthesis to molecularly tag RNA and DNA coming from the same cell. The integration of unique molecular identifiers (UMIs) or barcodes that span 4-8 base pairs and are added to sequences during reverse transcriptase step, and tag mRNA and DNA from specific cells to identify molecular counts coming from the same cell.[17,20]. The methods necessary for paralleled analysis to perform genome and transcriptome sequencing are made possible by the physical separation of polyadenylated mRNA (polyA mRNA) from DNA using biotinylated oligo-dT (deoxy-thymine) primers, which are used to separate DNA from RNA.[18,21]. After separation they are run through separate amplifications and sequencing.

In one aspect, methylation patterns and transcription patterns can be analyzed in the same cell. Epigenetic modifications can occur through DNA methylation, histone modification and alteration to microRNAs.

The term "methylation pattern" refers to the pattern of epigenetic modification by which DNA methyltransferase (DNMT) adds a methyl group to cysteine residues in a nucleic acid molecule. DNA methylation is one mechanism for modifying gene expression and is associated with a variety of cell phenotypes.[13] The upregulation of DMNTs (such as DNMT1, 3a and 3b) are higher in HCC patients than normal patient hepatocytes and involved in silencing tumor suppressors that facilitates HCC metastasis, invasion and proliferation.

The "pattern" of methylation can refer to the number and order of cysteine residues having attached methyl groups. A methylation pattern can include identifying the degree to which (e.g., the percentage of cysteine residues) a nucleic acid has cysteine residues with methyl groups.

The term "histone modification" can refer to phosphylation, ubiquitination, acetylation and methylation of promotors, enhancers, oncogenes and tumor suppressors. In one aspect, histone lysine methyltransferase and histone lysine demethyltransferase can alter gene expression through conformational changes to euchromatin and heterochromatin.[13]

In one aspect, histone methyltransferase on arginine or lysine residues, can add methyl groups to resides which can condense heterochomatin and inactivate gene expression of tumor suppressors.[13]

In another aspect, histone demethyltransferase on arginine or lysine resides, such as H3K9 and K27, can remove methyl groups from these residues, and facilitate upregulation of promoters, enhancers and oncogenes.[13]

The term "MicroRNAs" refers to non-coding RNAs that regulate gene expression at the post transcriptional level by binding to 3' untranslated regions (3-UTR).[22] Exosomes are elevated in HCC, for example high levels of exosomal micro RNA-103 (miR-103) are associated with vascular permeability and promotes metastasis.[13]

In another aspect, the nucleic acid is selected from the group consisting of at least one of miR-25, miR-26b-5p, miR-27a-3p, miR-30a, miR-30b, miR-320a, miR-1247-3p, miR-103, miR-345, miR-542-3p, miR-142, miR-630, miR-181a, miR-155, miR-199b-5p, miR-300, miR-216, miR-217, miR-1306-3p, miR-122, miR-140-5p, and miR-506, miR-148a.

In another aspect, the degree of methylation can be determined by measuring the level of methyltransferases in the exosome or circulating tumor cell. The methyltransferases can be selected from the group consisting of DNA methyltransferases, histone methyltransferases and histone demethyltransferase. The DNA methyltransferases can be selected from the group consisting of DNMT1, DNMT3a and DNMT3b. The histone methyltransferases can be selected from the group consisting of JARID1B, SETDB1, EHMT2, EZH2, SUV39H1, KDM4B, KDM5C, KDM6B.

In a further aspect, single-cell sequencing of the nucleic acid can be used to identify epigenetic-transcriptomic regions. The epigenetic-transcriptomic regions can be selected from the group consisting of at least one of liver-specific transcripts, HCC transcripts, oncogenes, somatic mutations and cancer hallmarks. The liver-specific transcripts can be selected from the group consisting of at least one of ALB, HP, FGB, FGG, and SERPINA1. HCC transcripts (also known as differentially expressed MSTRG transcripts) are selected from the group consisting of GBK2, NDUFB10, PARL, ZW10, Y1F1B, UPB1, TBC1D10C, GNA11, IQSEC1, COL15A1, and SLC30A6. The differentially expressed MSTRGs have a q value less than 0.05, which indicates less than a 5% chance that the differential expression occurred by chance. The oncogenes can be selected from the group consisting of at least one of HBV encoded X Protein (HBx), Non-structural protein 5a (Ns5A) and Ns3.

The somatic mutations and cancer hallmarks can be selected from the group consisting of at least one of AKT3, BCL2, BRAF, DENND4A, CCND2, CD244, CHD1, EEF2, FGF12, HK1, HRAS, IDH, KDR, KRAS, KLRK1, MTOR, MYC, NOS2, NOS3, NRAS, PIK3CA, PIK3R2, PSMB9, PTEN, RAET1L, RAG1, RAG2, RB1, SNAI2, TAP1, TAP2, TAPBP, TERC, TERT, TGFB1, TNFSF14, TNF, TP53, TWIST1, TWIST2, VEGFA, VEGFC, VEGFD, ZEB1, ZEB2, SMAD1, SMAD7, PNEN, PAK, N-Cadherin, E-Cadherin, VE-Cadherin, BIM, Slug, Wnt1, RhoGDI1, FBXL5, FAK, IRF1, ZOI, B4GALT3, and PBX3.

In another aspect, single cell sequencing can be conducted by RNA-Seq, DNA-Seq, Bisulfite-Seq (BS-Seq), Reduced Representation Bisulfite Sequencing, Methyl-Seq, Massively-Paralleled RNA-Seq, TAB-seq, Aba-seq, and/or Chip-Seq.

In a further method, the volume of the blood sample is from about 50 nanoliters to about 5 milliliters. The exosome or circulating tumor cell can be isolated from the blood sample by droplet based microfluidics. For example, a plurality of cells from the exosome and optionally encoded with an identifier. The identifier can be selected from the group consisting of at least one of at least one of liver specific transcripts, oncogenes, somatic mutations and cancer hallmarks as described herein.

In another aspect the nucleic acid is selected from the group consisting of DNA, RNA, and miRNA. In yet another aspect, the nucleic acid is DNA and the DNA is isolated from the blood sample by droplet based microfluidics.

In one aspect, the exosome or circulating tumor cell originates from a tissue selected from the group consisting of liver, blood, urine, stool, and saliva. The term "originates" refers to the primary or original tissue source of the exosome or circulating tumor. For example, if an exosome or circulating tumor cell originates from the lung and metastasizes to the liver, the primary or original tissue source would be the lung. In one aspect, the exosome or circulating tumor cell originates from the liver.

In yet another aspect, the patient has not been diagnosed with a liver cancer. For example, the patient can be routinely monitored to detect an early or late stage of liver cancer. The patient, for example, may have been diagnosed with a hepatitis infection but not yet developed liver cancer. In this aspect, the patient can be routinely monitored to detect an early stage of liver cancer and receive early treatment or other intervention.

In one aspect, the patient has been diagnosed with a liver cancer (e.g., hepatocellular carcinoma). In this aspect, the stage of liver cancer in the patient can be monitored to determine, for example, if a treatment or course of treatment is beneficial and determine if a patient is in remission.

Additional aspects provide kits comprising at least a first probe for identifying a surface marker in a protein sequence isolated from an exosome or circulating tumor cell and at least a second probe for identifying a methylation pattern in the nucleic acid, wherein the methylation pattern corresponds to the degree of methylation of the nucleic acid. The term "kit" refers to a collection of one or more of materials, reagents, and packaging material. A kit can be self-assembled or can be sold to a diagnostic laboratory or hospital. An exemplary kit can comprise one or more probes or other detection molecules for identifying a methylation pattern as described herein. Reagents for storing, transporting, and interrogating biological samples can be included in the kit. Instructions for use of the kit may also be included.

In one aspect, the first probe comprises an antibody capable of detecting a cell surface marker associated with a hepatocyte cell.

In another aspect, the at least a second probe comprises one or more probes capable of detecting miR-25, miR-26b-5p, miR-27a-3p, miR-30a, miR-30b, miR-320a, miR-1247-3p, miR-103, miR-345, miR-542-3p, miR-142, miR-630, miR-181a, miR-155, miR-199b-5p, miR-300, miR-216, miR-217, miR-106-3p, miR-122, miR-140-5p, and miR-506, miR-148a.

In yet another aspect, the at least a second probe is capable of detecting the level of methyltransferases (e.g., DNA methyltransferases and histone methyltransferases) in the exosome or circulating tumor cell compared to a control normal cell. The DNA methyltransferases can be selected from the group consisting of DNMT1, DNMT3a and DNMT3b. The histone methyltransferases can be selected from the group consisting of JARID1B, SETDB1, EHMT2, EZH2, SUV39H1, KDM4B, KDM5C, KDM6B.

In another aspect, the kit includes at least a third probe capable of identifying epigenetic-transcriptomic regions (liver specific transcripts, HCC transcripts, oncogenes, somatic mutations and cancer hallmarks).

The liver-specific transcripts can be selected from the group consisting of at least one of ALB, HP, FGB, FGG, and SERPINA1. HCC transcripts (also known as differentially expressed MSTRG transcripts) are selected from the group consisting of GBK2, NDUFB10, PARL, ZW10, Y1F1B, UPB1, TBC1D10C, GNA11, IQSEC1, COL15A1, and SLC30A6. The differentially expressed MSTRGs have a q value less than 0.05, which indicates less than a 5% chance that the differential expression occurred by chance. The oncogenes can be selected from the group consisting of at least one of HBV encoded X Protein (HBx), HCV core protein, Non-structural protein 5a (Ns5A) and Ns3.

The somatic mutations and cancer hallmarks can be selected from the group consisting of at least one of AKT3, BCL2, BRAF, DENND4A, CCND2, CD244, CHD1, EEF2, FGF12, HK1, HRAS, IDH, KDR, KRAS, KLRK1, MTOR, MYC, NOS2, NOS3, NRAS, PIK3CA, PIK3R2, PSMB9, PTEN, RAET1L, RAG1, RAG2, RB1, SNAI2, TAP1, TAP2, TAPBP, TERC, TERT, TGFB1, TNFSF14, TNF, TP53, TWIST1, TWIST2, VEGFA, VEGFC, VEGFD, ZEB1, ZEB2, SMAD1, SMAD7, PNEN, PAK, N-Cadherin, E-Cadherin, VE-Cadherin, BIM, Slug, Wntl, RhoGDI1, FBXL5, FAK, IRF1, ZOI, B4GALT3, and PBX3.

Methods of analyzing transcriptional expression and methylation patterns by isolating at least one exosome from peripheral blood cells obtained from a patient; applying a unique barcode to the at least one exosome to identify nucleic acid signals from the at least one exosome, wherein the nucleic acid comprises DNA and RNA; separating the DNA from the RNA; conducting single-cell RNA sequencing on the RNA and identifying transcriptional expression levels of at least one of oncogenes, somatic mutations, and cancer hallmarks in the at least one exosome; and conducting bisulfite conversion and single-cell TET associated bisulfite sequencing on the DNA and identifying methylation patterns of at least one of DMNTs, histones, and microRNA in the at least one exosome are provided.

The term "miR" refers to microRNAs or miRNAs, small, non-coding RNAs that can be silenced by CpG island hypermethylation. The hypermethylation and hypomethylation patterns or profiles can be a hallmark or characteristic of tumor types, metastases etc.

In a further aspect, the degree of methylation of the nucleic acid is determined by measuring the level of methyltransferases (e.g., DNA methyltransferases and histone methyltransferases/demethyltransferase) in the exosome or circulating tumor cell compared to a control normal cell. The level of methyltransferases can be measured by comparing normal tissue to disease states and assessing percent changes of methylation, using hierarchical clustering analysis, heatmap for visualization, pairwise supervised Principle Component Analysis (PCA) and percent methylation changes of healthy, compared to chronic hepatitis, compared to HCC samples to determine tumorigenic phenotype.[23] The methods to achieve these analyses are described below from sequences steps through bioinformatics analysis.

Multiple-omic sequencing of the transcriptome and the DNA methylome can be run in parallel in the same cell, which is called single cell methylation and transcription sequencing (scM&Tseq). During single sequencing after mRNA is physically separated from DNA, mRNA is followed in steps above and DNA is treated with bisulfite conversation to enable absolute quantification of the DNA methylome.[18] In brief, bisulfite sequencing (BS-Seq) synthetically converts cytosine to uracil, but does not convert methylated cytosine (5 mC) therefore 5 mC is sequenced as cytosine and unmethylated cytosines are sequenced as uracil.[18]

Methylated cytosine (denoted 5 mC) are controlled through various methyltransferases (such as DNA methyltransferases 1 or DNMT1).[19] 5 mC is involved in dysregulation of gene expression in various cancers.[24] Hydroxymethylated cytosine (5 hmC) is an intermediate of DNA methylation, specifically the oxidation product of Ten-eleven translocation methylcytosine dioxygenase 1 (TET1) enzyme that is involved in demethylation of gene bodies.[19, 24]. 5 hmC and 5 mC both regulate methylation patterns in aberrant gene expression and are distinctly involved in epigenetic reprogramming, furthermore they must be differentiated in order for accurate interrogation of gene regulation circuits.[19,24.]

Quantification of methylation patterns has faced limitations in the past due to low capture efficiency.[18] Recent advancements, such as post-bisulfate adaptor-tagging (PBAT) have increases efficiency from 10% to 50% capture of CpG sites. In the past, methods performed paired adaptor ligation first, followed by bisulfite conversation, and this order decreased measurement of methylated sites due to DNA degradation of adaptor ligated regions during bisulfite conversion. PBAT methods, however, perform bisulfite conversion prior to library preparation, which allows for better coverage of methylation in CpG regions, therefore DNA degradation does not affect fragmentation of adaptor ligated regions.[18]

BS-Seq can identify 5 mC effectively but cannot distinguish 5 mC from 5 hmC. Further alterations to the protocol, must use chemical affinity tags for 5 hmC.[18, 19] Restriction enzymes, such as TET1 can be used to distinguish 5 mC from 5 hmC through TET-associated bisulfite sequencing (TAB-Seq) which uses TET1 enzyme for conversion of 5 mC, but not 5 hmC. TAB-Seq blocks glycosylation of hydroxymethylated cytosines. This step subsequently allows the oxidation of only 5 mC (but not 5 hmC) to be converted to 5-formylcytosine and 5-carboxylcystine.[18,19] These steps are followed by deep sequencing techniques.

Comparison of healthy, verses chronic hepatitis, verses HCC hepatocyte derived samples will be compared for identification of epigenetic alterations. Analysis to hydromethylation, 5 mC and 5 hmC can be investigated through various bioinformatics pipelines, one such as Methylation INTegration (MINT) can process and analyze 5 mC/5 hmC data sets.[24] The pipeline uses command-line tools for quality control, methylation quantification and differential methylation patterns. Of interest, comparison modules are executed for Differentially Hydroxymethylated Regions (DhmR) and Differentially Methylated CpG regions (DMR) and results are quantified by strong, medium or weak differential that can be run through R Bioconductor (an open source genomic tool used for statistical programming).[24] DhmR and DMR can be measured through various models, including measuring log changes between normal, cirrhotic and HCC tissue; in our methods we will analyze differential changes of 5 mC/5 hmC and hydromethylated and changes indicate log changes in Beta greater than 0.2 will be further analyzed for statistical significance.

The differential methylation and demethylation can be analyzed by comparing percent changes in healthy verses chronic hepatitis verses HCC samples to determine percent methylation changes. A common analysis for methylation patterns uses average β (called β-values) which determines percent methylation and unmethylated regions. The analysis uses log ratio (denoted M) to determine methylation: $M = \log_2 (Max (M, 0))/Max (U, 0)$. In which, 0 indicates slightly methylated regions.[25] A negative M represents percent of methylated regions and a positive M represents unmethylated regions.[25] Hierarchical clustering analysis and pairwise supervised Principle Component Analysis (PCA) can be performed to quantify differential expression of 5 mC, 5 hmC and hypomethylated regions.[23,26] CpG regions with an absolute value (or change in β) greater than 0.2 (the standard threshold for statistically significant methylation changes) indicating that changes between the sample correlates to a confidence of 99%.[25]

Global percent methylation changes between normal, cirrhotic and HCC samples, indicate more similar methylation patterns between normal and HCC samples.[23,26] Cirrhotic samples indicate discrete methylation patterns with temporary methylation occurrences that are recovered after development of HCC. In other words, methylations patterns are more similar between normal and HCC samples, with discrete peaks during prolonged cirrhosis, indicating that differences between cirrhosis, normal, and HCC cells are subtle.

DNA methyltransferases are selected from the group consisting of DNMT1, DNMT3a and DNMT3b. Histone methyltransferases are selected from the group consisting of JARID1B, SETDB1, EHMT2, EZH2, SUV39H1, KDM4B, KDM5C, KDM6B.[13] The methods to analyze are as described above, using change in β, and differential expression of DhmR, DMR and hypomethylated regions.

In another aspect, single-cell sequencing of the nucleic acid can be used to identify epigenetic-transcriptomic regions. Through single cell sequencing of the genome and the transcriptome, known as G&T-sequencing, specifications and methods are described in depth below. The epigenetic-transcriptomic regions are selected from the group consisting of at least one of liver specific transcripts, HCC transcripts, oncogenes, somatic mutations and cancer hallmarks. Liver-specific transcripts are selected from the group consisting of at least one of ALB, HP, FGB, FGG, and SERPINA1 using methods described below for FPKM values to identify expression. HCC transcripts (also known as differentially expressed MSTRG transcripts) are selected from the group consisting of GBK2, NDUFB10, PARL, ZW10, Y1F1B, UPB1, TBC1D10C, GNA11, IQSEC1, COL15A1, and SLC30A6). The oncogenes can be selected from the group consisting of at least one of HBV encoded X Protein (HBx), HCV core protein, Non-structural protein 5a (Ns5A) and Ns3 using methods described below for FPKM values to identify differential expression.

Somatic mutations can be directly induced through the incorporation of HBV and HCV onto the human genome. Cancer hallmarks, subsequently, are the downstream consequences that are affected after aberrations to other genes (such as alterations to tumor suppressors or oncogenes have occurred). Although the terms somatic mutations and cancer hallmarks are separate mechanisms, they both represent a group of genes involved in the initiation of tumorigenesis and varying stages.

In one aspect, the volume of the blood sample is from about 50 nanoliters to about 5 milliliters. In another aspect, the exosome or circulating tumor cell can be isolated from the blood sample by droplet based microfluidics. A plurality of cells can be isolated from the exosome. In another aspect, each of the plurality of cells are encoded with an identifier. The identifier can be selected from the group consisting of at least one of liver specific transcripts, oncogenes, somatic mutations and cancer hallmarks.

In some aspects, common single cell library prep methods, lead to low capture of mRNA through previous steps, but effective strategies can enable higher capture. One example uses template switching during the second strand synthesis. For the first stand synthesis, cDNA is prepped by a modified version of the Moloney Murine Leukemia virus (M-MLV), which uses low RNAase H activity for reverse transcriptase. Then, second strand synthesis can either use poly(A) tailing or template switching followed by amplification.[17]

Template switching commonly called; "Switching mechanism at the 5' end of the RNA template" or (SMART-seq) enables higher mRNA capture efficiency coverage without the loss of strand specificity.[20] Template Switching Oligonucleotides (TSO) relies on 2-5 untemplated oligonucleotides added to the 3' end of cDNA during reverse transcriptase when the 5' is reached.[27] M-MLV is able to switch templates and synthesize the cDNA, at the TSO location. Smart-seq2 (the newest version of SMART-seq) uses TSO sequences with two riboguanosines located in the second and third positions, along with a modified guanosine which produces a locked nucleic acid (LNA). Synthetic LNAs allows for increased thermal stability and can anneal the untemplated 3' cDNA extension for higher coverage.[27]

RNA-Seq data and differential transcript analysis can be analyzed by various bioinformatics software programs. HiSAT, StringTie and Ballgown are open source tools that can measure abundance of differentially expressed genes and novel isoforms using R package and Bioconductor for statically analysis.[28] RNA-Seq data can be broken down into four steps; aligning raw reads to the genome, assembling reads into full length transcripts, quantifying both transcript and gene expression and finally analysis of district conditions. HiSAT maps reads to the genome, StringTie assembles the alignment for quantification of gene and transcript expression. Ballgown uses statistical modeling from StringTie output for the quantification and visualization of differentially expressed transcripts (DET) (including novel isoforms). The abundance of transcripts is quantified through Fragments Per Kilobase of transcripts mapped per Million mapped reads (or FPKM values). Ballgown outputs a data set showing p-values and q-values of fold changes between samples.[28]

Q-Values are a measurement of False-Positive Rates (FPR) when a q-value is lower it decreases the likelihood of a FPR.[29] The differentially expressed genes in our analysis will have q-value<0.05, which indicates that the differential expression of this group of genes between samples has statistical significant of less than a 5% chance that this result occurred by chance. Samples showing a log change greater than 0.2 can indicate a tumorigenic phenotype and can be further analyzed.[29]

In another aspect, the nucleic acid is DNA, and the DNA is isolated from the blood sample by droplet based microfluidics. The term "isolated" refers to sufficiently separating the nucleic acid from cells in blood or tissue such that the nucleic can be sequenced or identified by other means (e.g., labelled probe, chromatography, gel electrophoresis etc.). The term "droplet based microfluidics" refers to the method in which cells are isolated.

Further aspects provide novel methods and kits combining identifying the source of an exosome or circulating tumor cell, and determine the phenotype of the exosome or circulating tumor cell (e.g., normal, pre-tumorigenic, tumorigenic) by detecting at least one methylation pattern in a nucleic acid from the exosome or circulating tumor and/or detecting further transcriptional differences between a sample from a patient and a normal control cell.

Probes can be used to detect methylation patterns. In this aspect, the term "probe" refers to a molecule (nucleic acid, antibody, enzyme, or portions thereof) that can specifically detect the presence of and/or quantify the amount of a target molecule (e.g., nucleic acid, protein, etc.). The presence or amount of a target molecule can be compared to a normal (i.e., non-tumorigenic) exosome/cell to aid in determining the phenotype of the exosome or circulating tumor cell.

For example, a labelled DNA or RNA probe that is complementary to sequence of an RNA transcript or other nucleic molecule in an exosome or cell can be used to detect the presence and/or quantify the amount of a target molecule in the exosome or cell. In another example, a labelled antibody can be used to detect the presence of and/or quantify the amount of a target protein molecule (e.g., methyltransferase) to determine the degree of methylation of nucleic acid in the exosome or cell.

TABLE 1

Viral oncogenes, associated cancers, somatic mutations, and at risk populations.[1-4]

| Virus | Cancer Type(s) | Viral Oncogene Target | Downstream Targets and Cancer Hallmark Target | At Risk Population |
|---|---|---|---|---|
| Hepatitis B Virus | Hepatocellular Carcinoma | HBV encoded X proteins (HBx) | ROS p53/mtntp53, hTERT, Rb, and TGF-β mutated Ras | Chronic hepatitis infection, currently HCC is on the rise in the US |
| Hepatitis C Virus | Hepatocellular Carcinoma | HCV encoded core proteins Nonstructural protein 5A and 3 (Ns5A and Ns3) | ROS p53/mtntp53 hTERT, Rb, and TGF-β | Chronic hepatitis infection, currently on the rise in the US |

Table 1 provides exemplary viral oncogene targets and downstream targets and cancer hallmark targets for Hepatitis B and Hepatitis C. Probes directed to these targets can be used in aspects described herein to identify methylation patterns. Table 1 describes cancer types, targets (e.g., associated viral oncogenes), cancer hallmark targets, and populations associated with hepatitis B and hepatitis C infections.

Associated viral oncogenes can be used as cellular biomarkers to determine initiation of tumorigenesis. Downstream targets associated with the oncogenes, major cancer hallmarks can be used as targets to determine stage of cancer and at risk populations. For example, p53, Rb, hTERT, mutated Ras, and Nf-kB transcription factor overexpression are common downstream targets associated with hepatitis induced cancers.[1-3,30-32]

Table 2 provides an overview of Hepatitis B Virus (HBV) lytic viral oncogenes, common somatic mutations, and associated genetic hallmarks. Probes directed to these targets can be used in aspects described herein.[1-4]

TABLE 2

| Lytic Viral Oncogenes | Somatic Mutations | Cancer Hallmarks |
|---|---|---|
| HBV Encoded X Protein (HBx) | TGF-B Ras mutant p53/wt-p53 hTERT Rb | See Table 3 HBV is associated with 10 hallmarks |

TABLE 2-continued

| Lytic Viral Oncogenes | Somatic Mutations | Cancer Hallmarks |
|---|---|---|
| | Upregulates mir-181 (promotes "stemness") HIF1-a Ang2, VEGF, MMP P13K, JAK/STAT, Nf-kB, Hedgehog | |

Table 3 provide an exemplary overview of Hepatitis C Virus (HCV) associated lytic viral oncogenes, common somatic mutations, and associated genetic hallmarks. Probes directed to these targets can be used in aspects described herein.[1, 31, 33-45]

TABLE 3

| Lytic Viral Oncogenes | Common Somatic Mutations | Cancer Hallmarks |
|---|---|---|
| HCV Encoded core protein(s): Non-structural protein 5a (Ns5A) Non-structural protein 3 (Ns3) | TGF-B KRAS NRAS HRAS TP53 Overexpression mutant p53 Downregulation of wt-p53 hTERT Rb gene (downregulation) Mir-181a HIF1-a (Hypoxia Inducible Factor F1-a overexpression Ang-2 (Angiopoitein-2 activated via HIF1A) HGF (Hepatocyte growth factor) | See Table 4 HCV associated with all 10 hallmarks |

Table 4 describes exemplary major cancer hallmarks and most common overexpressed/downregulated mutations. Probes directed to these targets can be used in aspects described herein.[1, 31, 33-45]

TABLE 4

| Ten Cancer Hallmark/ Brief Description | Genes Upregulation/ Overexpres si on | Genes Downregulated/ Inhibited genes |
|---|---|---|
| Genomic Instability Mutations to caretaker genes, loss of telomeric repeats, chromosomal reengagements and subsequent deletions | Recombinase activating gene 1/2 RAG1 RAG2 | |
| Resisting cell death Avoiding apoptotic pathways | NF-xB (nuclear factor kappa light chain enhancer) Tumor necrosis factor | BCL-2 (anti apoptotic) |

TABLE 4-continued

| Ten Cancer Hallmark/ Brief Description | Genes Upregulation/ Overexpression | Genes Downregulated/ Inhibited genes |
|---|---|---|
| Deregulating Cellular Energetics Reprogramming of cellular energetic and metabolic pathways | Warburg effect: Isocitrate dehydrogenase (IDH) | Glycolytic enzymes: HK PK PFK |
| Sustaining Proliferative Signaling Infinite number of replications | B-RAF (p94), mutant to V600E P13KCA (both overexpressed/ then downregulated) MTOR -mTORC1 and mTORC2 both controlled by Mammalian target of rapamycin complex gene Mutated Ras: KRAS_homosapiens NRAS_homosapiens HRAS_homosapiens MYC (including 8:14 translocations) C-MYC (control of Ig Heavy Chain Enhancer) -MYC in conjunction with: rearranged immunoglobulin heavy chain enhancer | Mutant PTEN (mutant version) |
| Evading Growth Suppressors Mutation and dysregulation of tumor suppressors, including mutations followed by overexpression of tumor suppressors | Mutant p53 (mutant p53) Elongation factor 2 (EF2) | Downregulation of wild type p53 Retinoblastoma (Rb) gene |
| Avoiding Immune Destruction Deficiency, as well as support from innate and adaptive immunity. (Overabundance of T Cells/B Cells) | NK gene (NK cell receptors): CD244 KLRK1 (killer cell lectin like receptor K1) MHC-1 genes (overexpression induces inhibitory signal) TAP1 TAP2 TAPBP PSMB9 RAETIL | |
| Enabling Replicative Immortality Unlimited replications without consequences | TERC (telomere RNA component) hTERT (*unrelated to telomere maintenance, exhibit alternative functions) hTERT (mRNA isoform) C.) Human Telomerase Reverse Transcriptase (hTERT) | |
| Tumor Promoting Inflammation Inflammation to enhance tumor progression | Reactive oxygen species genes: VEG-F iNOS (inducible nitric oxide synthase) NOS2/NOS3 P13K-AKT-mTOR genes: AKT3 gene PIK3R2 gene CCND2 gene Ras-MAPK (see RAS mutations above in proliferative signaling) BCL-12 (also known as BLC-6) | PTEN gene (inactivation) |
| Activating invasion and metastasis Metastasis typically | N-cadherin also known as cadherin-2 gene (CDN2 gene) Transcriptional factors: Snail2/Slug, Twist1 and Twist2 Zeb1 and Zeb2 | E-cadherin (CHD1) (Dysregulation/ mutant) |
| Inducing Angiogenesis Creation of new blood cells | VEG-F VEF homologs [KRD, VEGF-C, VEGF-D,] Basic fibroblast growth factor (bFGF) Transforming growth factor (TGF)-α, TGF-β, Tumor necrosis factor (TNF)-α, platelet-derived | |

The data used in FIGS. 1 and 2 (below) used raw read RNA-Seq data from Hlady et al. (2019) that made public a retrospective transcriptomic study of patients with Chronic Hepatitis C and HCC.[46] The study followed 4 patients with chronic hepatitis C, hepatocyte samples were analyzed when the patients had cirrhosis (but had not yet developed HCC) using RNA-Seq through Illumina HiSeq platform. Liver tissue (hepatocytes) from the same 4 patients were collected several years later (at different intervals) after patients had developed HCC and analyzed again through RNA-Seq.[46]

Differential expression was analyzed on Seven Bridges Cancer Genomics Cloud (CGC) using HiSAT2, StringTie and Ballgown to map reads, assemble transcriptions and quantify differential gene expression.[28,59] Steps from RNA-Seq bioinformatics pipeline are followed as mentioned in the methods. For differential expression output low abundance transcripts (transcripts that have similar expression values) were filtered out if they did not surpass a $\log_2$ value change. Post filtration, cirrhosis and HCC samples were shown to have more similar FPKM of genes and transcripts expressed. In general, cirrhosis has higher abundance of FPKM for genes and transcripts than HCC, indicating that cirrhosis undergoes certain incubation criteria in order to induce HCC (data not shown), but these ideas will require further validation.

As shown in FIG. 1a, exon-intron structures were compared between differentially expressed transcripts of cirrhotic-normal samples, HCC-normal samples and cirrhotic-HCC samples. The top five differentially expressed genes were analyzed for each.

Figure 1B:
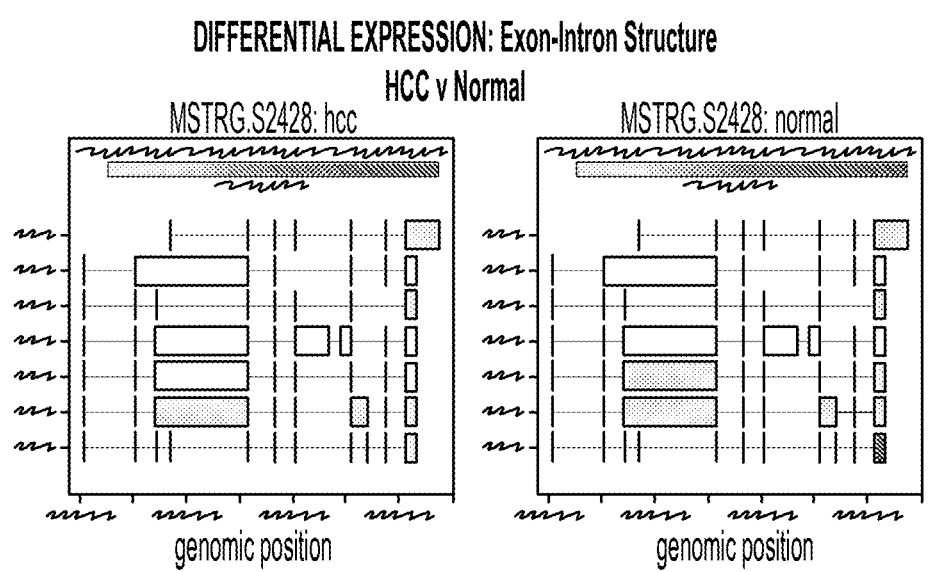

FIG. 1b shows a zoomed in version of the exon-intron structures from MSTRG. These structures occurred in the top 5 of all analyses and correspond to genes and transcripts that were unrecognizable from the reference genome files input into StringTie. This indicates that these transcripts may be novel isoforms that may have yet to be identified in the development of HCC. StringTie was run several times to align reads to reference files of known transcripts to confirm the novelty of the structures. MSTRG thus represent potential novel transcripts differentially expressed between healthy and diseased HCC tissues.

Figure 2A:
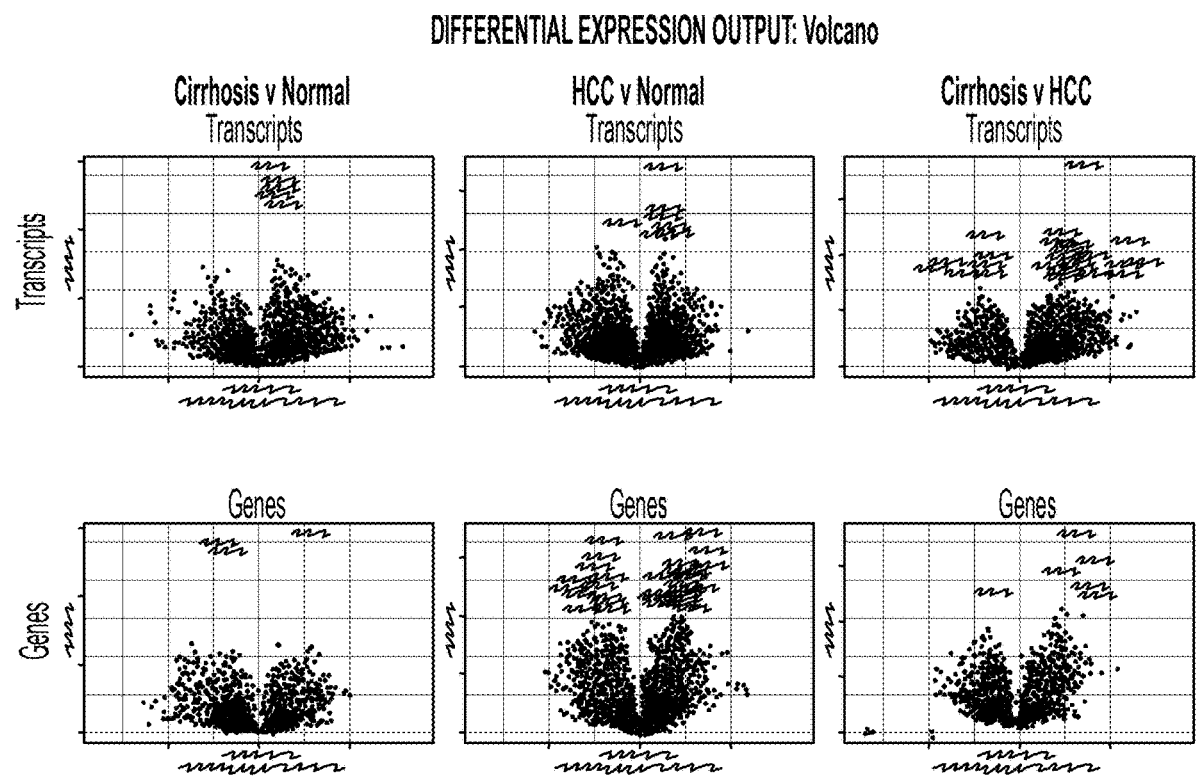
FIGS. 2a-2b provides exemplary Volcano plots depicting differential transcript and gene expression between normal samples verses cirrhotic samples verses HCC samples, indicating MSTRG potential novel gene transcripts.

FIG. 2a shows the results of differential gene expression analysis and plotted through volcano plots for genes and transcripts of Cirrhotic verses Normal, HCC verses Normal and Cirrhotic verses HCC to visualize changes in gene and transcript expression.

Figure 2B:
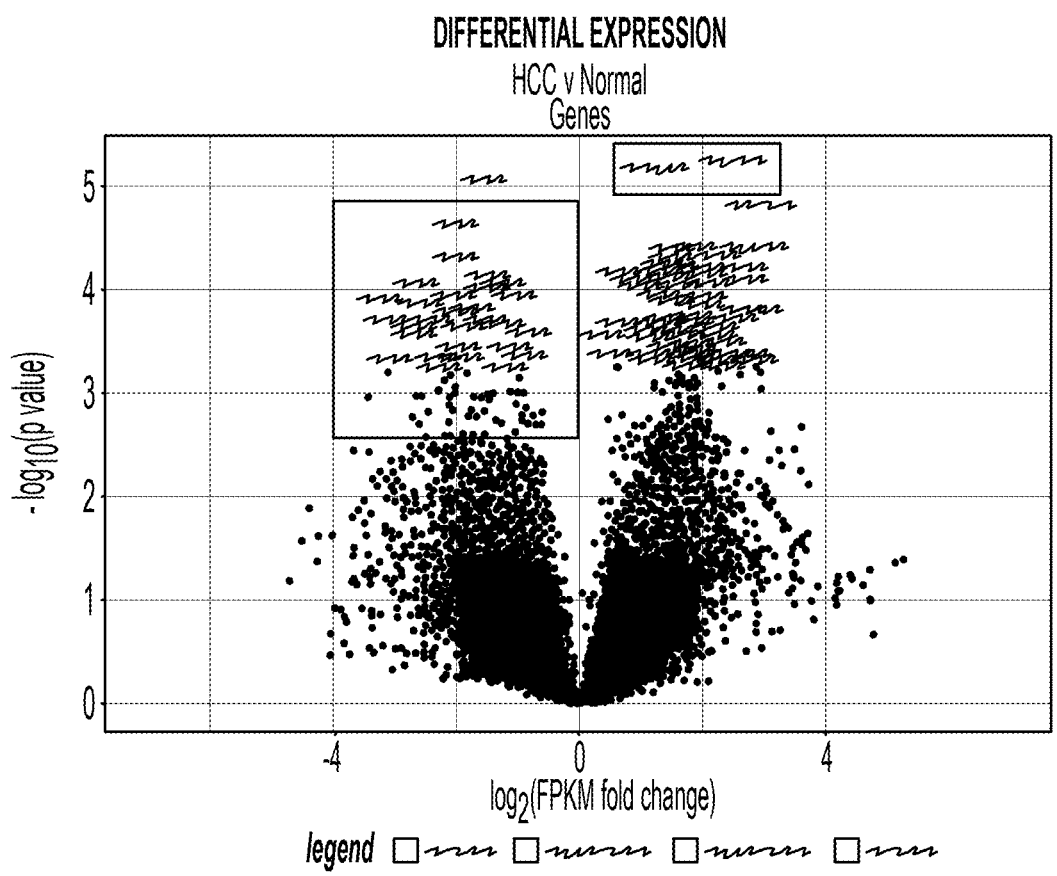

FIG. 2*b* provides Q-Values are a measurement of False-Positive Rates (FPR) when a q-value is lower it decreases the likelihood of a false positive. The differentially expressed genes (HCC transcripts) in the red box (GBK2, NDUFB10, PARL, ZW10, Y1F1B, UPB1, TBC1D10C, GNA11, IQSEC1, COL15A1, and SLC30A6) have a q-value<0.05, this indicates that the differential expression of this group of genes between the normal and HCC tissue is statistically significant and has less than a 5% chance that this result occurred by chance. These genes are also referred to as MSTRG transcripts or differentially expressed MSTRG transcripts. This is further validated by the genes (cancer hallmark targets) differentially expressed in the green box, which were genes that are known and specifically targeted because they are involved in HCC development. The genes identified in the green box (ALB, HP, FGB, FGG, and SERPINA1) serve as a control transcripts to confirm that the MSTRG are tumorigenic phenotype.

Figure 3:
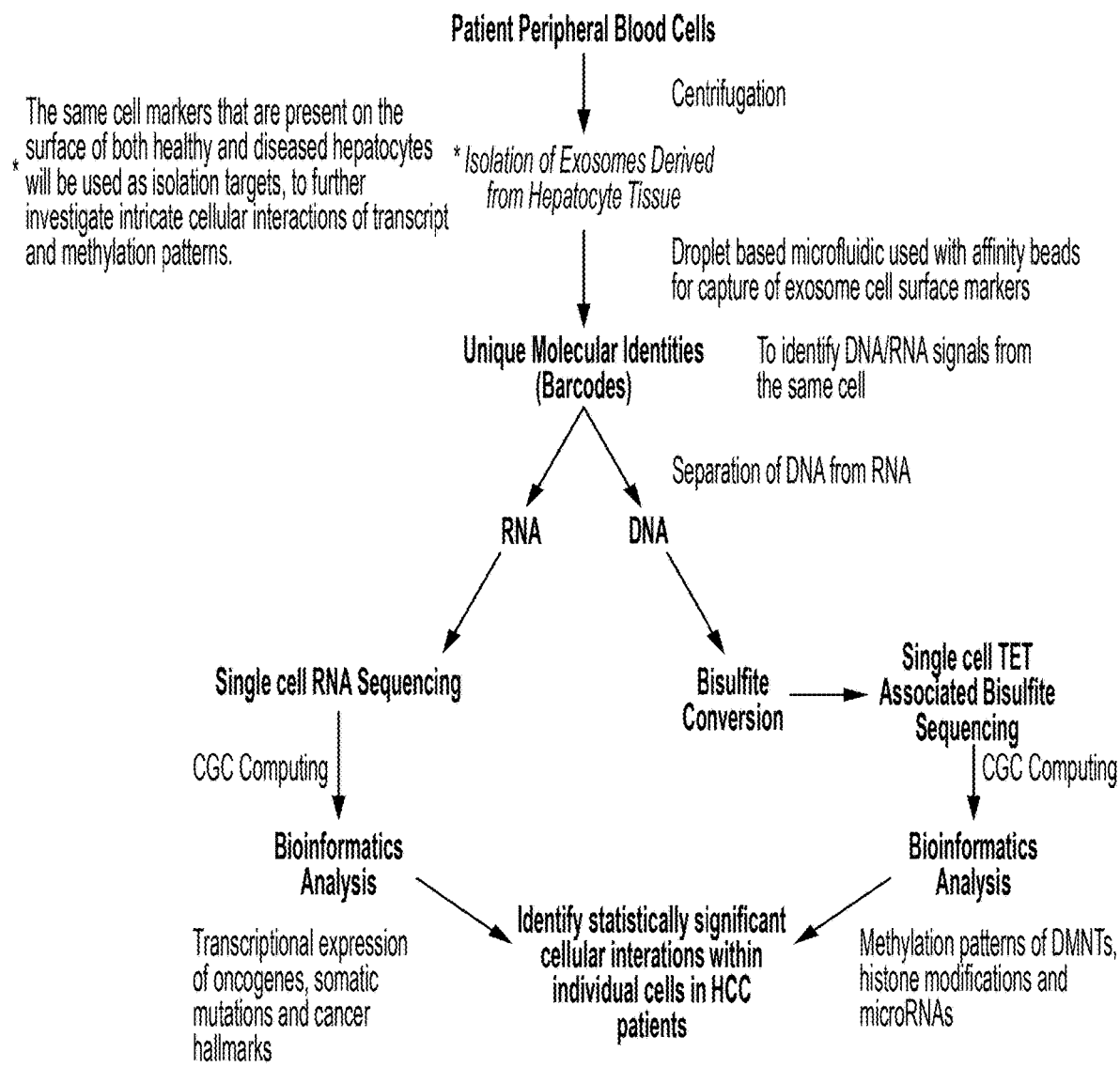
FIG. 3 provides a flow chart with exemplary steps of methods described herein from isolation of hepatocytes in peripheral blood cells through single cell sequencing and analysis of cellular interactions.

FIG. 3 provides a flow diagram showing exemplary steps for individual cell analysis in accordance with aspects described herein, from the isolation of peripheral blood cells to analysis of single cell interactions. In this example, peripheral blood cells are obtained from the patient, then exosomes are isolated using affinity bead capture microfluidics to target surface markers on the outside of hepatocyte derived exosomes. In this example, cell surface markers are not used to identify aberrant mutations, but rather to target markers that that can capture both healthy and diseased hepatocyte tissue. In other words, the cell surface markers are used to identify tissue source rather than a state of the cell (e.g., normal vs. HCC).

After isolation unique molecular identifies (UMIs) are used to barcode DNA and RNA coming from the same cell, this is necessary because running paralleled single cell sequencing of the genome and transcriptome are physically separated to run each analysis. Thus, RNA is physically separated from DNA using biotinylated deoxy-thymine primers, then RNA is sequenced through conventional RNA seq and then analyzed for transcriptional patterns. DNA is first treated with bisulfite conversion followed by post-bisulfite adaptor tagging (PBAT) with TET1 enzyme in order to quantify methylation patterns. Transcriptional patterns and methylation patterns are analyzed through computing tools on the Cancer Genomics Cloud. Finally, analysis of interactions runs statistical modeling to determine that the events of methylation patterns and transcriptional patterns will both occur in a given population of HCC patients.[59] Ultimately, using a multitude of transcriptional and methylation interactions that occur in the same cell to diagnose HCC.[17,18,20]

EXAMPLES

Example 1—Theoretical Models of Viral Oncogene Expression Patterns

Viral oncogene expression levels and tracking patterns of corresponding pathways have yet to be implemented into early diagnostics and could significantly benefit patients. While signaling molecules are known, they have not been utilized to serve patients effectively for early disease diagnosis.

In one aspect, three models that relate to assessing viral mRNA expression patterns that indicate induction of tumorigenesis are provided: (1) determining expression levels of an oncogene during tumor development, (2) determining the substantially constant expression level of an oncogene level over a predetermined period of time, and (3) determining the oncogenic expression level threshold for inducing tumorigenesis. In one aspect the "oncogenic threshold" is the level of oncogene expression that indicates induction of tumorigenesis.

Increasing levels of viral oncogene expression can be a direct cause of cancer progression through the stages of cancer. Increasing magnitude of oncogene expression levels past the oncogenetic threshold indicates greater risk of inducing somatic mutations, contributing to progression through disease stages and poor prognosis.

In another aspect, stages of cancer can be chronological responses to viral oncogene expression that reach an oncogenetic threshold, resulting in chronological responses to the disease. In this aspect, the level of viral oncogene expression does not change, but remains substantially constant, and the natural consequences of sustained expression leads to increased somatic mutations and hallmarks that are continuously reinforced through presence of specific and substantially unchanged viral oncogene expression.

In another aspect, viral oncogene expression levels reach a threshold and induce somatic mutations. After induction of somatic mutations occur, the expression of viral oncogenes is no longer relevant for progression through stages of cancer. Instead, progression through cancer stages are caused by expression of mutated somatic genes that do not require reinforcement of viral oncogene stimulus.

Example 2—Gaps for Detection of Viral Cancer

Aspects described herein analyze gaps in early viral cancer detection and provide targets for determining risk assessment of patient acquiring a suspected disease. Each method will analyze the degree of viral tumorigenesis, in which expression of viral oncogenes cause somatic mutations, leading to development of cancer hallmarks that can be detected to determine early onset of tumorigenesis.

Gaps for Periodic Detection of the Transcriptome

Aspects described herein are directed to novel methods and compositions for periodically profiling transcriptional expression to determine how expression changes over time to determine disease progression. Although RNA-sequencing technologies have advanced rapidly in the last few decades, there is a necessity for new services to offer patients medical analyses of their transcriptome to target and analyze specified genes using the tools of genomics, genomics and artificial intelligence, precision oncology, and bioinformatics and genome sequencing.

Gaps for Hepatocellular Carcinoma Caused by HBV/HCV

Development of HCC is a clear consequence of persistent HBV/HCV infection, but it is not known whether transformation from abnormal cells to hepatocellular carcinomas is caused by a chronological response to sustained oncogene expression or is a direct result of increased oncogene expression. Although consequences of persistent fibrosis may appear to be chronological responses to lytic infection, various stage and/or aggressiveness of HCC may contribute to changes in viral oncogene expression patterns.

The accumulation of fibrosis (scarring of hepatocyte tissue) may persist for a specific amount of time, but transformation of cells from fibrosis, to cirrhosis, to HCC may be a direct result of achieving viral oncogenetic threshold (or the magnitude of viral oncogene expression).

In one aspect, methods of diagnosing HCC caused by hepatitis B virus are provided by determining at the level of transcriptional expression and length of expression of viral oncogene HBx in order to induce somatic mutations.

In another aspect, methods of diagnosing HCC are provided by determining transcriptional activity of somatic mutations associated with HBx, which include, but are not limited to, detection of downregulation of Rb gene, and mutation followed by overexpression of p53 gene and Ras gene.

In another aspect, methods of diagnosing HCC are provided by determining transcriptional activity of cancer hallmarks, which include, but are not limited to, hTERT, TGF-β and ROS. These aspects including, but are not limited to, determining expression level or copy number variant of oncogenes sufficient to indicate inducement of cancer hallmarks.

In another aspect, methods of and compositions for detecting viral oncogenes, somatic mutations, and cancer hallmarks are provided by periodically tracking the level and duration of viral oncogene expression in order to determine changes at varying stages, and the aggressiveness of the cancer. The term "periodically" as used herein refers to, for example daily, monthly, weekly, bi-monthly, semi-annually, annually, every two years, every three years, every five years, etc.

In another aspect, methods of and compositions for detecting expression of viral oncogenes, somatic mutations and cancer hallmarks are provided by comparing the expression of viral oncogenes to expression of viral oncogenes in patient derived cell (PDC) lines (available from sources including, but not limited to, American Type Culture Collection (ATCC), Manassas, Virginia). HCC HBV cell lines useful in aspects described herein include, but are not limited to, SNU-398 samples.[47]

Methods for detection of hepatocellular carcinoma (HCC) caused by hepatitis B include, obtaining a tissue sample, identifying a methylation pattern corresponding to a degree of methylation of a nucleic acid derived from the tissue sample, measuring the level of nucleic acid expression of HBx oncogene in tissue sample, and measuring nucleic acid expression of somatic mutations correlated to HBx (e.g., mutated p53, mutated Ras gene and downregulation of Rb gene). Measurement of cancer hallmarks (i.e., genes) that can be transcriptionally detected include, but are not limited to; hTERT, TGF-β and ROS. In these aspects, it is believed that the probability of developing HCC is increased by about 88% if the level of HBx oncogene is increased two-fold as compared to a control HCC patient derived cell line sample.

In another aspect, methods of diagnosing HCC caused by hepatitis C, are provided by determining the level of transcriptional expression and length of expression of viral oncogenes HCV encoded core protein, Ns5a and Ns3 sufficient to induce somatic mutations.

In another aspect, methods of diagnosing HCC are provided by determining transcriptional activity of somatic mutations associated with vial oncogenes (HCV ended core protein, Ns5a and Ns3) including somatic mutations (e.g., downregulation of Rb and overexpression of mutant p53).

In another aspect, methods of diagnosing HCC caused by hepatitis C are provided by determining transcriptional activity of HCC hallmarks (e.g., hTERT, TGF-β and ROS).

In another aspect, methods of diagnosing cancers are provided by identifying a methylation pattern corresponding to a degree of methylation of a nucleic acid derived from a tissue sample, detecting viral oncogene, somatic mutations, and cancer hallmarks periodically in order to determine changes at varying cancer stages and identifying the aggressiveness of the cancer.

In another aspect, expression of viral oncogenes, somatic mutations and cancer hallmarks are compared to PDC lines (e.g., available from cell line repositories such as ATCC). HCC cell lines specific for HCV include, but are not limited to, C3A [HepG2/C3A] samples.[47]

Methods for detection of HCC caused by hepatitis C include, obtaining a tissue sample, measuring the level of nucleic acid expression of viral oncogenes HCV encoded core protein in the tissue sample, measuring nucleic acid expression of somatic mutations correlated to oncogenes (e.g., mutated p53 and downregulation of Rb). Measurement of cancer hallmarks that can be transcriptionally detected include, but are not limited to, hTERT, TGF-β and ROS. In these aspects, the probability of developing HCC from HCV is increased by about 88% if the level of viral oncogene is increased two-fold as compared to a control tissue sample.

Example 3—Kits and Methods of Viral Oncogene Detection

In one aspect, the subject/patient can be evaluated for cancers induced by HCV or HBV. In certain non-limiting embodiments, aspects described herein include obtaining tissue samples from a tissue of origin, (e.g., blood plasma, serum, saliva, urine, and stool). Tissue of origin, as used herein, can refer to the location from which the primary tumor arises. Other suitable biological samples include, but are not limited to, tissue samples, liquid biopsy, fresh, and/or frozen samples. In this aspect, the tissue samples can be analyzed using, for example multiplexed probes for oncogenic mutations, somatic mutations, and cancer hallmarks.

In certain non-limiting embodiments, viral oncogenes, somatic mutations and associated genetic cancer hallmarks are detected through various sequencing methods.

In certain non-limiting embodiments, viral oncogenes, somatic mutations and associated genetic cancer hallmarks can be detected by RNA sequencing, such as, but not limited to, targeted amplicon RNA sequencing, and/or whole transcriptome sequencing.[48]

In certain non-limiting embodiments, viral oncogenes, somatic mutations and associated genetic cancer hallmarks can be detected by DNA sequencing, such as, but not limited to, targeted genome sequencing, and/or whole genome sequencing.[48]

In certain non-limiting embodiments, viral oncogenes, somatic mutations and associated genetic cancer hallmarks are detected using nucleic acid probe-based hybridization methods.

In certain non-limiting embodiments, viral oncogenes, somatic mutations and associated genetic cancer hallmarks can be detected by hybridization probe based analysis, such as, but not limited to, Polymerase Chain Reaction (PCR), Fluorescent in Situ Hybridization and DNA/RNA microarrays, DNA/RNA sequencing.[49,55]

Diagnostic Methods for Assessing Risk

Aspects described herein target viral oncogenes, associated somatic mutations and associated cancer genetic hallmarks to evaluate risk of developing various viral-induced cancers (e.g., hepatocellular carcinoma).

In one aspect, a custom oligonucleotide captured probe is designed for the identification of a specific region of interest.

The custom oligonucleotide can be configured to align to related sequences in a range between about 70% alignment upwards of about 90% alignment in order to identify conserved regions in the target of interest. In another aspect, primer and probes can be designed using the National Center for Biotechnology Information (NCBI) genomic screening software through Basic Local Alignment Sequence Tool (BLAST) to identity sequences and enable visualization of sequences to target. NCBI BLAST is a resource that allows deep analysis of genomically complete organisms to target specific genes, including Eukaryotic, Prokaryotic, Viral genomes as well as transposable elements that transition between the major divisions (i.e. viral oncogenes).[53]

In another aspect, the primers and probes can be designed using Geneious software, an online bioinformatics platform that allows for analysis of genes and genomes for use of next generation sequencing techniques, such as identification of conserved genomic regions through sequence alignment.[51] MAFFT is a plugin program that works within Geneious, and can be used to determine highly conserved nucleotide regions for specified genes. MAFFT facilitates sequence alignment, which can be performed by extracting whole genome sequences, followed by executing alignments within the program. In another aspect, identification of sequences through BLAST followed by alignment using Geneious is repeated until highly conserved regions are found for primers and probes based upon genomic target characteristics.[51]

In certain non-limiting aspects, design of primers and probes for targeted regions can be developed using other online computational techniques. Oligonucleotides can be designed using, for example, Oligo-Architecture Sigma Aldrich, which is a computational tool that supports design of primers and probes for region of interest based on certain parameters. Parameters that can be used in designing primers and probes include, but are not limited to, melting point (Tm), target length of amplicon, length of probe, GC content, and additional modifications to design specified.[52] Design features can also include incorporating synthetic nucleotides to increase hybridization, such as locked nucleic acids (LNAs) within the probe target region. The design features can use single fluorescence for detection, such as SYRB Green, or Dual-Labeled probes among other variations of probes dependent upon the experimental design of the assay.[52]

In certain non-limiting aspects, once probes and primers are designed using computational tools, accurate design can be confirmed using NCBI Nucleotide-Blast to ensure that the probes target the correct region of interest. For example, the oligonucleotides can be entered into BLAST nucleotide either through a FASTA file or letters comprising the sequence, and the resulting hits can be searched and analyzed.[53]

In certain non-limiting aspects, computationally-designing probes of interest for each viral oncogene can be synthesized using Targeted Amplicon RNA sequencing. In another aspect, total RNA is prepared from tissue samples for each tissue involved, the target region of interest is flanked by a quencher (or a primer), RNA is reverse transcribed, and then poly-adenylated RNA is anchored with complementary DNA (cDNA) oligonucleotide adaptors.[48] In this aspect, hybridization is allowed to proceed until the probes are fully bound to cDNA. Next, covalently bound cDNA undergoes extension and ligation at the region of interest, yielding a library of template molecules. PCR amplification can be used to produce clonal clusters followed by sequencing (e.g., using Next Generation Sequencing, which is defined as modern, high throughput, deep sequencing technologies) to determine expression for probes of interest.[48]

In certain, non-limiting aspects, fluorescent probes can be used to analyze samples (e.g., linear fluorescence resonance energy transfer (FRET) probes), in which two linear oligonucleotides hybridize to the same nucleic acid region and form a pair between the donor and acceptor fluorophore.[49] Signals from FRET probes are only detected when both probes hybridize to target RNA. FRET pairing differentiates between background noise of unbound regions and target regions of probe.

In certain, non-limiting aspects, Dual Labeled Probes can be used to analyze samples. Dual-labeled probes can be designed with two fluorescence dyes; a reporter dye and a quencher.[54] For example, a reported dye can be located on the 5' end, and during the elongation phase (e.g., by Taqman polymerase) probes target and bind to regions of interest. The quencher, located on the 5' end, inhibits the natural occurrence of fluorescence emission by FRET (fluorescence resonance energy transfer) until hydrolysis occurs. During hydrolysis, the reporter probe is released leading to an increase of signal strength measured by florescence signal.[54] The signal strength is directly proportional to the amount of DNA present in sample.

In certain non-limiting aspects, methods of detection include, but are not limited to, molecular beacons such as, stem-loop oligonucleotide hairpin probes for dual labeling of reporter fluorophore and quencher on opposite ends. Molecular beacons are sensitive and upon detection of target can increase signal 200 fold. This probe florescence method favors a suitable application for potentially low expression for targets of viral oncogenes and somatic mutations.[49]

In certain non-limiting aspects, multiplexing probes can be used for amplification of two or more gene targets within a single RNA-Seq array. As used herein, the term "multiplexing" refers to mixing more than one probe pair within a single experiment to determine expression of two or more gene targets.[55]

In certain non-limiting aspects, incorporating synthetic nucleotides into the probe sequence can increase stability, probe hybridization to target region, and enhance sensitivity.[54] For example, locked nucleic acids (LNA) containing 2'-O, 4'-C methylene bridges that lock the 3'-endo conformation region of the ribose ring to support hybridization can be used. Furthermore, incorporating synthetic nucleotides into amplicon allows for effective multiplexing assays.[54]

In one aspect, multiplexing, is used to analyze exosome or cfDNA in PBCs (peripheral blood cells) to determine tissue of origin, and also interrogate expression of a specified gene from that tissue. In this aspect, the tissue of origin, (such as the liver) can be identified based on specific gene expression in nucleosomes.[12] Thus, in this aspect, PBCs can be used as a "liquid biopsy" to determine where expression of genes occur by simultaneously determining tissue of origin, and genes (such as viral oncogenes) expressed in that specified tissue. Use of a liquid biopsy is less stressful and less expensive than outpatient surgery.

In certain non-limiting aspects, the Human Protein Atlas (HPA) database can be used to determine epigenetic biomarkers of genes that are expressed in specified tissues.[56] The HPA is an open source online database that maps human's proteins based on mass spectrometry of antibodies, and compiles information based upon proteomics, transcriptomics and genomic data.[56]

Periodically tracking changes in expression of viral oncogenes, somatic mutations and cancer hallmarks listed below and determining the degree of methylation of a nucleic acid derived from a tissue sample will facilitate a method for early tumorigenesis intervention.

The probes developed for HBV include, but are not limited to, HBx encoded X protein (HBx), ROS, p53/mutant p53, hTERT, R, TGF-β and mutated Ras.

The probes developed for HCV include, but are not limited to, the transcripts that encode for HCV Encoded Core proteins, Nonstructural protein 5A (Ns5A), Ns3, ROS, p53/mutant p53, hTERT, Rb and TGF-β.

Example 4—Primers/Probes

The probes below reflect an exemplary design made using NCBI-Probe that uses Primer3 interface, which is a computational tool that is used to design oligonucleotide primers and probes for hybridization assays.[57,58,60] Nucleotides sequences extracted and analyzed from NCBI Gene can be used in NCBI-Probe to design probes for regions of interest. The amplicons here depict general probes that can be used in conjunction with, but not limited to, various single labeled and/or dual labeled probe methodologies, as well as multiplexing techniques and the use of synthetic nucleotide sequences to increase sensitivity and specificity of hybridization.

DNMT1:
F:
    SEQ ID NO: 1
CGACTACATCAAAGGCAGCAA

R:
    SEQ ID NO: 141
TTGCTGCCTTTGATGTAGTCG

DNMT3a:
F:
    SEQ ID NO: 2
CCACCAGAAGAAGAGAAGAAT

R:
    SEQ ID NO: 142
ATTCTTCTCTTCTTCTGGTGG

DNMT3b:
F:
    SEQ ID NO: 3
CCGAGCGATTTCAAATTTCCCT

R:
    SEQ ID NO: 143
GAGTGGGTGGGAGGGG

JARID1B:
F:
    SEQ ID NO: 4
CGAGATGGAATTAACAGTCTT

R:
    SEQ ID NO: 144
AAGACTGTTAATTCCATCTCG

SETDB1:
F:
    SEQ ID NO: 5
CAGTGACTAATTGTGAGTCTT

R:
    SEQ ID NO: 145
AAGACTCACAATTAGTCACTG

EHMT2:
F:
    SEQ ID NO: 6
ACTATGGCAACATCAGCCG

R:
    SEQ ID NO: 146
AGCTCATCCCCAGTCCG

EZH2:
F:
    SEQ ID NO: 7
GAAACAGCTGCCTTAGCTTCA

R:
    SEQ ID NO: 147
TGAAGCTAAGGCAGCTGTTTC

SUV39H1:
F:
    SEQ ID NO: 8
GCACAAGTTTGCCTACAATG

R:
    SEQ ID NO: 148
TTCTGGACTACACGGTTTGG

KDM4B:
F:
    SEQ ID NO: 9
GCGGCAGACGTATGATGACAT

R:
    SEQ ID NO: 149
ATGTCATCATACGTCTGCCGC

KDM5C:
F:
    SEQ ID NO: 10
TCGCAGAGAAATCGGGCATTT

R:
    SEQ ID NO: 150
AAATGCCCGATTTCTCTGCGA

KDM6B:
F:
    SEQ ID NO: 11
TCAGGGGCCTGGCTGGTTCA

R:
    SEQ ID NO: 151
GTTCACCGCTCGCCTCCACC miR-21:
F:
    SEQ ID NO: 12
CGGCGGTAGCTTATCAGACTGA

R:
    SEQ ID NO: 152
CTGGTGTCGTGGAGTCGGCAATTC miR-25:
F:
    SEQ ID NO: 13
GAGCTAGCACTTCCCGAGC

R:
    SEQ ID NO: 153
TAGCTGTCTGCCCCTTGTCT miR-26b:
F:
    SEQ ID NO: 14
CCTCGGATGGGAATTGGATA

R:
    SEQ ID NO: 154
AGAGGCGCACAGGAAGGA

-continued miR-27a:
F:
TCCTGTCACAAATCACATTGC SEQ ID NO: 15

R:
AGAGTTGGGGATCAGGGC SEQ ID NO: 155 miR-30a:
F:
GTAAACATCCTCGACTGGAAGCT SEQ ID NO: 16

R:
GCTGCAAACATCCGACTGAA SEQ ID NO: 156 miR-30b:
F:
ACCCAACTCACTTCTGCCTT SEQ ID NO: 17

R:
TTCCTCTATAAGCATACTGTTTTCTG SEQ ID NO: 157 miR-103:
F:
GCTTCTTTACAGTGCTGCCT SEQ ID NO: 18

R:
TTCATAGCCCTGTACAATGCT SEQ ID NO: 158 miR-122:
F:
CTTAGGTGGGACTCGCCTC SEQ ID NO: 19

R:
ACCCAGAGTGCTAGGGGTTT SEQ ID NO: 159 miR-140:
F:
CAGTGGTTTTACCCTATGGTAGG SEQ ID NO: 20

R:
CGTGGTTCTACCCTGTGGTAG SEQ ID NO: 160 miR-142:
Full:
TGTAGTGTTTCCTACTTTATGGATGTAGTGTTTCCTACTTTATGGA SEQ ID NO: 21 miR-148a:
F:
GAGGAAGACAGCACGTTTGGT SEQ ID NO: 22

R:
AAAGGCGCAGCGACGT SEQ ID NO: 161 miR-155:
F:
TTCTGCAAATCAAATCATTAGC SEQ ID NO: 23

R:
TTCTTCCTCCATAAAATGGGG SEQ ID NO: 162 miR-181a:
F:
TCAAAGACATTTTCTCAGACATTCA SEQ ID NO: 24

R:
GATTGCAGGACCATTTCTGG SEQ ID NO: 163 miR-300:
F:
UAUGCAAGGGCAAGCUCUCUUC SEQ ID NO: 25 miR-320a:
F:
CGCCTTCTCTTCCCGGT SEQ ID NO: 26

R:
TTCGCCCTCTCAACCCA SEQ ID NO: 164 miR-345:
F:
CTGACTCCTAGTCCAGGGCT SEQ ID NO: 27

R:
CTCCAGACCCCTCGTTCA SEQ ID NO: 165 miR-506:
F:
AGTGCCTTATTCAGGAAGGTGT SEQ ID NO: 28

R:
CCACCACAAATGTTGTCCATGT SEQ ID NO: 166 miR-630:
F:
GATCCAAGACTGGCTGACTTC SEQ ID NO: 29

R:
GTGCTCTATTACCGGGGTTT SEQ ID NO: 167 miR-199b:
F:
CACCGGATGGACAGACA SEQ ID NO: 30

R:
CGGTCCAGCTCTCCAGT SEQ ID NO: 168 miR-216:
F:
TGGCTTAATCTCAGCTGGCA SEQ ID NO: 31

R:
TGAGGGCTAGGAAATTGCTCT SEQ ID NO: 169 miR-1306-3p:
F:
TGCCCCATGAACAGTCTCCACCAC SEQ ID NO: 32

R:
CCCCATAGGCCTACCCCATTACCA SEQ ID NO: 170

HbX1:
F:
TGTCAACAACCGACCTTGATT SEQ ID NO: 33

R:
TCAAGGTCGGTTGTTGACATT SEQ ID NO: 171

-continued

HbX2:
F:
GCTGCTCGGGTGTGCTGCCTT                 SEQ ID NO: 34

R:
GGCAGCACACCCGAGCAGCTT                 SEQ ID NO: 172

HGF:
F:
CTGCAGATGAGTGTGCCAAC                  SEQ ID NO: 35

R:
CCAGTAGCATCGTTTTCTTGACT               SEQ ID NO: 173

Rb:
F:
GCTGTTTCTGGGGATTAAATAAGAC             SEQ ID NO: 36

R:
CCGCAGGGAATATCTGGCT                   SEQ ID NO: 174

HIF1-a:
F:
CTGATGACCAGCAACTTGATT                 SEQ ID NO: 37

R:
TCAAGTTGCTGGTCATCAGTT                 SEQ ID NO: 175

Ang2:
F:
ATGGCGATGAGCCCAGGTCCTTTGTTC           SEQ ID NO: 38

R:
CTATGGACTGATAAAAGACTCATCAAA           SEQ ID NO: 176

MMP:
F:
AGTTCCCGGAGTGAGTTGAA                  SEQ ID NO: 39

R:
CTCCACTCCTCCCTTTCCTC                  SEQ ID NO: 177

P13K:
F:
ACGGCTCAATGTTTGGAGAC                  SEQ ID NO: 40

R:
TGGAGTGAACACCAAAACCA                  SEQ ID NO: 178

Nf-Kb:
F:
CCACAAGACAGAAGCTGAAG                  SEQ ID NO: 41

R:
AGATACTATCTGTAAGTGAACC                SEQ ID NO: 179

Hedgehog:
F:
GACCGAAGAGTTTGTAGAGAA                 SEQ ID NO: 42

R:
TTCTCTACAAACTCTTCGGTC                 SEQ ID NO: 180

VEGF:
F:
ATCCGCAGACGTGTAAATGTTCCT              SEQ ID NO: 43

R:
TCACCGCCTTGGCTTGTCAC                  SEQ ID NO: 181

TGFB:
F:
TGACGTCACTGGAGTTGTACGG                SEQ ID NO: 44

R:
GGTTCATGTCATGGATGGTGC                 SEQ ID NO: 182

KRAS:
F:
GCCTGCTGAAAATGACTGAATATAAAC           SEQ ID NO: 45

R:
TGATTCTGAATTAGCTGTATCGTCAAG           SEQ ID NO: 183

NRAS:
F:
CCCGCTACGTAATCAGTCGG                  SEQ ID NO: 46

R:
CATGACTCGTGGTTCGGAGG                  SEQ ID NO: 184

HRAS:
F:
ATGACGGAATATAAGCTGGTG                 SEQ ID NO: 47

R:
GGAGAGCACACACTTGCAGCTCAT              SEQ ID NO: 185

TP53:
F;
ACGACGGTGACACGCTTCCCTG                SEQ ID NO: 48

R:
CGCTAGGATCTGACTGCGGCTC                SEQ ID NO: 186 hTERT:
F:
GCGGGCACAGACGCCCAGGACCGAGCT           SEQ ID NO: 49

R:
GCGGAAAGGAAGGGGAGGGGCTGGGA            SEQ ID NO: 187

Ns5A:
Full:
AGCTCTAGATGCCATCCGTGCCTCTGAGATCCCATTTCACGCTGAAGGCC   SEQ ID NO: 50

Ns3:
F:
GCGGGATACAATATTTAGCTT                 SEQ ID NO: 51

R:
GCTAAATATTGTATCCCGCTT                 SEQ ID NO: 188

Core:
F:
CAAGACTGCTAGCCGAGTAGTGTTGGGTCG        SEQ ID NO: 52

-continued

R:
TCGGGCACGAGACAVGCTGTGATATATG
SEQ ID NO: 189

RAG1:
F:
CAGGACTGTGAAAGCCATCACGGG
SEQ ID NO: 53

R:
CTGGAAAATCTGCCTCCCCGTGAT
SEQ ID NO: 190

RAG2:
F:
GCCATGATCTACTGCTCTCAT
SEQ ID NO: 54

R:
ATGAGAGCAGTAGATCATGGC
SEQ ID NO: 191

TGF:
F:
GCTCCAGAAGTTGCTTGTGC
SEQ ID NO: 55

R:
AACCAGAGGGCTGTTGATGG
SEQ ID NO: 192

IDH1:
F:
GCTGCAGTGGGACCACTATT
SEQ ID NO: 56

R:
TGTGGCCTTGTACTGCAGAG
SEQ ID NO: 193

BRAF (p.94):
F:
AGCTTATGTCAGGGGCTTTG
SEQ ID NO: 57

R:
AGAGAGCGTGCCAATAACTC
SEQ ID NO: 194

MTOR:
F:
CTGGGGCTTTGTGGTACGAG
SEQ ID NO: 58

R:
GGCCATTGACAGAGACGACA
SEQ ID NO: 195

MYC:
F:
GAGCCCCTGGTGCTCCATGAG
SEQ ID NO: 59

R:
AGGACTCTGACACTGTCCAACTTG
SEQ ID NO: 196

C-MYC:
F:
GCTCTCCATCCTATGTTGCGG
SEQ ID NO: 60

R:
TCCAAGTAACTCGGTCATCATCT
SEQ ID NO: 197

BCL2:
F:
CTGAGAGAGGCAGGCGATG
SEQ ID NO: 61

R:
CGATGCGACCCCAGTTTAC
SEQ ID NO: 198

EF2:
F:
GCGATCATGAATTTCAAGAAA
SEQ ID NO: 62

R:
TTTCTTGAAATTCATGATCGC
SEQ ID NO: 199

NK:
F:
CUACGUGACUCAUCCGAAATT
SEQ ID NO: 63

R:
UUUCGGAUGAGUCACGUAGAT
SEQ ID NO: 200

CD244:
F:
CCCTTCCTTCAATAGCACTAT
SEQ ID NO: 64

R:
ATAGTGCTATTGAAGGAAGGG
SEQ ID NO: 201

KLRK1:
F:
TGATGTGATAAACCGTGGTG
SEQ ID NO: 65

R:
TGGATCGGGCAAGGAAA
SEQ ID NO: 202

TAP1:
F:
CGATACCTTCACTCGAAACTT
SEQ ID NO: 66

R:
AAGTTTCGAGTGAAGGTATCG
SEQ ID NO: 203

TAP2:
F:
GATGAGTAACTGGCTTCCTTT
SEQ ID NO: 67

R:
AAAGGAAGCCAGTTACTCATC
SEQ ID NO: 204

PSMB9:
F:
CATCGAGTCATCTTGGGCAAT
SEQ ID NO: 68

R:
ATTGCCCAAGATGACTCGATG
SEQ ID NO: 205

RAET1L:
F:
GCTGGAGAATTACACACCCAA
SEQ ID NO: 69

R:
TGGGTGTGTAATTCTCCAGC
SEQ ID NO: 206

NOS2:
F:
ACATCGACCCGTCCACAGTAT
SEQ ID NO: 70

NOS3:
F:
CTGTGGTCTGGTGCTGGTC    SEQ ID NO: 71

R:
TGGGCAACTTGAAGAGTGTG    SEQ ID NO: 208

AKT3:
F
AGAAACCTCAAGATGTGGATT    SEQ ID NO: 72

R:
ATCCACATCTTGAGGTTTCT    SEQ ID NO: 209

PIK3R2:
F:
GAAAGAGATGCAAAGGATCCT    SEQ ID NO: 73

R:
AGGATCCTTTGCATCTCTTTC    SEQ ID NO: 210

CCND2:
F:
AGGAACTGTGTACGCCATTTA    SEQ ID NO: 74

R:
TAAATGGCGTACACAGTTCCT    SEQ ID NO: 211

Snail2:
F:
CTTTTTCTTGCCCTCACTGC    SEQ ID NO: 75

R:
ACAGCAGCCAGATTCCTCAT    SEQ ID NO: 212

Twist1:
F:
GGTCCATGTCCGCGTCCCAC    SEQ ID NO: 76

R:
AATGACATCTAGGTCTCCGGCCCTG    SEQ ID NO: 213

Twist2:
F:
GATTCAGGAACACATTTATG    SEQ ID NO: 77

R:
CATAAATGTGTTCCTGAATCT    SEQ ID NO: 214

Zeb1:
F:
GATGACCTGCCAACAGACCA    SEQ ID NO: 78

R:
CCCCAGGATTTCTTGCCCTT    SEQ ID NO: 215

Zeb2:
F:
CATGCGAACTGCCATCTG    SEQ ID NO: 79

R:
CAGAGGGGTAGGCTTGTCTC    SEQ ID NO: 207

R:
TATGCCTCTCGAGCTGGG    SEQ ID NO: 216

VEGF-C:
F:
TGCCAGCAACACTACCACAG    SEQ ID NO: 80

R:
GTGATTATTCCACATGTAATTGGTG    SEQ ID NO: 217

VEGF-D:
F:
AGGAAGGAGATTGGGTGAATC    SEQ ID NO: 81

R:
GCACCAAGGGGAAAAATTA    SEQ ID NO: 218

Bfgf:
F:
AGAGCGACCCTCACATCAAG    SEQ ID NO: 82

R:
ACTGCCCAGTTCGTTTCAGT    SEQ ID NO: 219

TNT:
F:
CCAGGGACCTCTCTCTAATCAGC    SEQ ID NO: 83

R:
CTCAGCTTGAGGGTTTGCTACAA    SEQ ID NO: 220

CHD1:
F:
CCATCGTGATTGGGATCACTA    SEQ ID NO: 84

R:
TAGTGATCCCAATCACGATGG    SEQ ID NO: 221

Liver-specific transcripts:
ALB:
F:
CGCTCATAGTTCGTTACACC    SEQ ID NO: 85

R:
CCAGGGACAGATAGTCTTCA    SEQ ID NO: 222

HP:
F:
GACCAATGCATAAGGCATTAT    SEQ ID NO: 86

R:
ATAATGCCTTATGCATTGGTC    SEQ ID NO: 223

FGB:
F:
CGTGTGCTTCGTTCAATCCTA    SEQ ID NO: 87

R:
TAGGATTGAACGAAGCACACG    SEQ ID NO: 224

FGG:
F:
GGCTGGGAAATGATGAGAAGAT    SEQ ID NO: 88

-continued

R:
CACAGTTGCCTTCAAACTTATC SEQ ID NO: 225

SERPINA1:
F:
GTGCCTATGATGAAGCGTTTA SEQ ID NO: 89

R:
TAAACGCTTCATCATAGGCAC SEQ ID NO: 226

Top MSTRGs in normal vs. cirrhosis
GRK2:
F:
GAGCGATAAGTTCACACGGTT SEQ ID NO: 90

R:
AACCGTGTGAACTTATCGCTC SEQ ID NO: 227

NDUFB10:
F:
GCAGAACTGTATCAAGGAAGT SEQ ID NO: 91

R:
ACTTCCTTGATACAGTTCTGC SEQ ID NO: 228

PARL:
F:
CCACAGGAAGATATGGACCAT SEQ ID NO: 92

R:
TGGTCCATATCTTCCTGTGG SEQ ID NO: 229

Top MSTRGs in HCC vs. Cirrhosis
ZW10:
F:
CAGGCCTACAGGTTCCAAGA SEQ ID NO: 93

R:
CTGGAAAGATGGAGGCAGC SEQ ID NO: 230

YIF1B:
F:
CATCACCAAGCTCAAGTATTA SEQ ID NO: 94

R:
TAATACTTGAGCTTGGTGATG SEQ ID NO: 231

UPB1:
F:
CTAGTTGCTAAGCTCGACCTA SEQ ID NO: 95

R:
TAGGTCGAGCTTAGCAACTAG SEQ ID NO: 232

Top MSTRGs in HCC vs. Cirrhosis
TBC1D10C:
F:
CTGAGAGGACCATGGACTTAG SEQ ID NO: 96

R:
CTAAGTCCATGGTCCTCTCAG SEQ ID NO: 233

GNA11:
F:
CGACCTGGAGAACATCATCTT SEQ ID NO: 97

R:
AAGATGATGTTCTCCAGGTCG SEQ ID NO: 234

IQSEC1:
F:
GAAGAAATTCACCGATGACCT SEQ ID NO: 98

R:
AGGTCATCGGTGAATTTCTTC SEQ ID NO: 235

COL15A1:
F:
CCTTTGATGGTCGAGACATAA SEQ ID NO: 99

R:
TTATGTCTCGACCATCAAAGG SEQ ID NO: 236

SLC30A6:
F:
CGGGAAGATTATTAGTTGGTA SEQ ID NO: 100

R:
ACCAACTAATAATCTTCCCG SEQ ID NO: 237

TFIP11:
F:
CCTGGGTTGGAAGTCGATGTT SEQ ID NO: 101

R:
ACATCGACTTCCAACCCAGG SEQ ID NO: 238

TAF5L:
F:
CCTGCCAAGAGAACAGACTAT SEQ ID NO: 102

R:
ATAGTCTGTTCTCTTGGCAGG SEQ ID NO: 239

YEATS4:
F:
GCTAACATTAGGAGCCTATAA SEQ ID NO: 103

R:
TTATAGGCTCCTAATGTTAGC SEQ ID NO: 240

SNX7:
F:
TGAGGAGAATATCCATTA SEQ ID NO: 104

R:
TAATAATGGATATTCTCCTCA SEQ ID NO: 241

MRPL36:
F:
CGGTGGTACGTCTACTGTAAA SEQ ID NO: 105

-continued

R:
TTTACAGTAGACGTACCACCG  SEQ ID NO: 242

PUDP:
F:
GTTATGGGTAAGAAGGCATTA  SEQ ID NO: 106

R:
TAATGCCTTCTTACCCATAAC  SEQ ID NO: 243

TSPAN7:
F:
GCAGACTTACAATGGCAATGA  SEQ ID NO: 107

R:
TCATTGCCATTGTAAGTCTGC  SEQ ID NO: 244

MYH9:
F:
GTGTGGCTGACGTAGTTGTATGTA  SEQ ID NO: 108

R:
GTAGATGAGCCCTGAGTAGTAACG  SEQ ID NO: 245

UBE2E1:
F:
CCTCCTTTCTATCTGCTCACT  SEQ ID NO: 109

R:
AGTGAGCAGATAGAAAGGAGG  SEQ ID NO: 246

UXS1:
F:
CCACCCTCAAAGTGAGGATTA  SEQ ID NO: 110

R:
TAATCCTCACTTTGAGGGTGG  SEQ ID NO: 247

PAK1:
F:
GTACAATAACTTGCCTGAAAT  SEQ ID NO: 111

R:
ATTTCAGGCAAGTTATTGTAC  SEQ ID NO: 248

GMPS:
F:
CCTACAGTTACGTGTGTGGAA  SEQ ID NO: 112

R:
TTCCACACACGTAACTGTAGG  SEQ ID NO: 249

PPDPF:
F:
GCAAGCAGACCTTCGCATCAA  SEQ ID NO: 113

R:
TTGATGCGAAGGTCTGCTTGC  SEQ ID NO: 250

ADCK3:
F:
TACCACCAGGACCAGTCATC  SEQ ID NO: 114

R:
GCCAGACCTCCAAAGTTAGC  SEQ ID NO: 251

INTS1:
F:
ACGGCCTTCAACACCAGAA  SEQ ID NO: 115

R:
CATTCTGGTGTTGAAGGCCGT  SEQ ID NO: 252

FGF4:
F:
CAAGCTCTATGGCTCGCCCTT  SEQ ID NO: 116

R:
AGGGCGAGCCATAGAGCTTG  SEQ ID NO: 253

PUSL1:
F:
CTATCTTGTGTACTTCCA  SEQ ID NO: 117

R:
TACTGGAAGTACACAAGATAG  SEQ ID NO: 254

DENND4A:
F:
CAGATGAACGTATTTCCTGTT  SEQ ID NO: 118

R:
AACAGGAAATACGTTCATCTG  SEQ ID NO: 255

FGF12:
F:
CTACACTCTCTTCAATCTAAT  SEQ ID NO: 119

R:
ATTAGATTGAAGAGAGTGTAG  SEQ ID NO: 256

HK1:
F:
CGCCATTCCTATTGAAATCAT  SEQ ID NO: 120

R:
ATGATTTCAATAGGAATGGCG  SEQ ID NO: 257

PIK3CA:
F:
TGGGGTAAAGGGAATCAAAAG  SEQ ID NO: 121

R:
CCTATGCAATCGGTCTTTGC  SEQ ID NO: 258

KDR:
F:
GTGGTCTCTCTGGTTGTGTAT  SEQ ID NO: 122

R:
ATACACAACCAGAGAGACCAC  SEQ ID NO: 259

PTEN:
F:
GTCATTTCATTTCTTTTTCTTTTCT  SEQ ID NO: 123

-continued

R:
CTGCACGCTCTATACTGCAAATG SEQ ID NO: 260

TAPBP:
F:
CCTGAGCTCTATCTCAGTGTA SEQ ID NO: 124

R:
TACACTGAGATAGAGCTCAGG SEQ ID NO: 261

TNFSF14:
F:
GTGCTGGATGAACGCCTGGTT SEQ ID NO: 125

R:
AACCAGGCGTTCATCCAGCAC SEQ ID NO: 262

TNF:
F:
GGCCAAGCCCTGGTATGAG SEQ ID NO: 126

R:
TAGTCGGGCCGATTGATCTC SEQ ID NO: 263

SMAD1:
F:
AGTTCTTACTCAAATGGGTTCA SEQ ID NO: 127

R:
AGGCTCCTTTGTCAGTTCTC SEQ ID NO: 264

SMAD7:
F:
ATTCCCAACTTCTTCTGGAG SEQ ID NO: 128

R:
TGGACACAGTAGAGCCTC SEQ ID NO: 265

PAK:
F:
GACTTTGTTGTAATAGATCCC SEQ ID NO: 129

R:
AAGAACAAACCTAAACCTAAA SEQ ID NO: 266

CDH2:
F:
CATCCTGAAGCAAAAGATTTAATGAC SEQ ID NO: 130

R:
TGGTAATTTAGAATTCTGTCCCTTTATTC SEQ ID NO: 267

CDH1:
F:
CCCACCACGTACAAGGGTC SEQ ID NO: 131

R:
CTGGGGTATTGGGGGCATC SEQ ID NO: 268

CDH5:
F:
AAGATGCTGGCTGAGCTGTACG SEQ ID NO: 132

-continued

R:
GATCCAGGTTGCAATGAGGTTG SEQ ID NO: 269

BIM:
F:
TTCTTGCAGCCACCCTGC SEQ ID NO: 133

R:
CTTGCGTTTCTCAGTCCGA SEQ ID NO: 270

Wnt1:
F:
AATCCAGAACACAACCTTGTC SEQ ID NO: 134

R:
CAAGGTTGTGTTCTGGATTCT SEQ ID NO: 271

RhoGDI1:
F:
GATGGTGTCAAGGAAGTGTTC SEQ ID NO: 135

R:
GAACACTTCCTTGACACCATC SEQ ID NO: 271

FBXL5:
F:
GTCAGAACACTCCACAGGTAT SEQ ID NO: 136

R:
ATACCTGTGGAGTGTTCTGAC SEQ ID NO: 273

FAK:
F:
CCACCTGGGCCAGTATTAT SEQ ID NO: 137

R:
ATAATACTGGCCCAGGTGG SEQ ID NO: 274

IRF1:
F:
GCGTGTCTTCACAGATCTGAA SEQ ID NO: 138

R:
TTCAGATCTGTGAAGACACGC SEQ ID NO: 275

B4GALT3:
F:
CCAGGCTGGAAATGGAACATT SEQ ID NO: 139

R:
AATGTTCCATTTCCAGCCTGG SEQ ID NO: 276

PBX3:
F:
CACACAGAACTGGAGAAATAT SEQ ID NO: 140

R:
ATATTTCTCCAGTTCTGTGTG SEQ ID NO: 277

F = Forward, R = Reverse

REFERENCES

1. Mesri, E. A., Feitelson, M. A., & Munger, K. (2014). Human viral oncogenesis: a cancer hallmarks analysis. Cell host & microbe, 15(3), 266-282.
2. Zemel, R., Issachar, A., and Tur-Kaspa, R. (2011). The role of oncogenic viruses in the pathogenesis of hepatocellular carcinoma. Clin. Liver Dis. 15, 261-279, vii-x.
3. Jeong, S. W., Jang, J. Y., and Chung, R. T. (2012). Hepatitis C virus and hepatocarcinogenesis. Clin Mol Hepatol 18, 347-356.
4. Bialecki, E. S., & Di Bisceglie, A. M. (2005). Diagnosis of hepatocellular carcinoma. HPB: The Official Journal of the International Hepato Pancreato Biliary Association, 7(1), 26-34. http://doi.org/10.1080/13651820410024049
5. Heimbach, J. K., Kulik, L. M., Finn, R. S., Sirlin, C. B., Abecassis, M. M., Roberts, L. R., . . . & Marrero, J. A. (2018). Aasld guidelines for the treatment of hepatocellular carcinoma. Hepatology, 67(1), 358-380.
6. Cirrhosis. (2018). American Association for Clinical Chemistry. Retrieved from shttps://labtestsonline.org/conditions/cirrhosis
7. Song, D. S., & Bae, S. H. (2012). Changes of guidelines diagnosing hepatocellular carcinoma during the last ten-year period. Clinical and Molecular Hepatology, 18(3), 258-267. http://doi.org/10.3350/cmh.2012.18.3.258
8. Peng, Y., Qi, X., & Guo, X. (2016). Child-Pugh Versus MELD Score for the Assessment of Prognosis in Liver Cirrhosis: A Systematic Review and Meta-Analysis of Observational Studies. Medicine, 95(8), e2877. http://doi.org/10.1097/MD.0000000000002877
9. Sofosbuvir (Solvaldi). (2018). Hepatitis C Online. Retrieved from https://www.hepatitisc.uw.edu/page/treatment/drugs/sofosbuvir-drug
10. De Oliveria Andrade, Luis Jesuino et al. "Association between hepatitis C and hepatocellular carcinoma." Journal of global infectious diseases vol. 1,1 (2009): 33-7. doi:10.4103/0974-777X.52979
11. Liew et al. (2006). "The peripheral blood transcriptome dynamically reflects system wide biology: a potential diagnostic tool" J Lab Clinical Medicine. 1 47:(3).
12. Snyder, M. W., Kircher, M., Hill, A. J., Daza, R. M., & Shendure, J. (2016). Cell-free DNA Comprises an In Vivo Nucleosome Footprint that Informs Its Tissues-Of-Origin. Cell, 164(1), 57-68.
13. Han, T. S., Ban, H. S., Hur, K., & Cho, H. S. (2018). The epigenetic regulation of HCC metastasis. International journal of molecular sciences, 19(12), 3978.
14. Zeringer, E., Barta, T., Li, M., & Vlassov, A. V. (2015). Strategies for isolation of exosomes. Cold Spring Harbor Protocols, 2015(4), pdb-top074476.
15. Braicu, C., Tomuleasa, C., Monroig, P., Cucuianu, A., Berindan-Neagoe, I., & Calin, G. A. (2015). Exosomes as divine messengers: are they the Hermes of modern molecular oncology?. Cell death and differentiation, 22(1), 34.
16. Zhang, W., Xia, W., Lv, Z., tin, Y., Ni, C., & Yang, L. (2017). Liquid biopsy for cancer: circulating tumor cells, circulating free DNA or exosomes?. Cellular Physiology and Biochemistry, 41(2), 755-768.
17. Hwang, B., Lee, J. H., & Bang, D. (2018). Single-cell RNA sequencing technologies and bioinformatics pipelines, Experimental & molecular medicine, 50(8), 96.
18. Clark, S. J., Lee, H. J., Smallwood, S. A., Kelsey, G., & Reik, W. (2016). Single-cell epigenomics: powerful new methods for understanding gene regulation and cell identity. Genome biology, 17(1), 72.
19. Sun, Z., Terragni, J., Borgaro, J. G., Liu, Y., Yu, L., Guan, S., . . . & Pradhan, S. (2013). High-resolution enzymatic mapping of genomic 5-hydroxymethylcytosine in mouse embryonic stem cells. Cell reports, 3(2), 567-576.
20. Hague, A., Engel, J., Teichmann, S. A., & Lönnberg, T. (2017). A practical guide to single-cell RNA-sequencing for biomedical research and clinical applications. Genome medicine, 9(1), 75.
21. Macaulay, I. C., Haerty, W., Kumar, P., Li, Y. I., Hu, T. X., Teng, M. J., . . . & Smith, M. (2015). G&T-seq: parallel sequencing of single-cell genomes and transcriptomes. Nature methods, 12(6), 519.
22. Qi, J., Wang, J., Katayama, H., Sen, S., &. Liu, S. M. (2013). Circulating microRNAs (cmiRNAs) as novel potential biomarkers for hepatocellular carcinoma. Neoplasma, 60(2), 135.
23. Ammerpohl, O., Pratschke, J., Schafmayer, C., Haake, A., Faber, W., von Kampen, O., . . . & Röcken, C. (2012). Distinct DNA methylation patterns in cirrhotic liver and hepatocellular carcinoma. International journal of cancer, 30(6), 1319-1328.
24. Cavalcante, R. G., Patil, S., Park, Y., Rozek, L. S., & Sailor, M. A. (2017). Integrating DNA methylation and hydroxymethylation data with the mint pipeline. Cancer research, 77(21), e27-e30.
25. Wilhelm-Benartzi, C. S., Koestler, D. C., Karagas, M. R., Flanagan, J. M., Christensen, B. C., Kelsey, K. T., . . . & Brown, R. (2013). Review of processing and analysis methods for DNA methylation array data. British journal of cancer, 109(6), 1394.
26. Hlady, R. A., Zhou, D., Puszyk, W., Roberts, L. R., Liu, C., & Robertson, K. D. (2017). Initiation of aberrant DNA methylation patterns and heterogeneity in precancerous lesions of human hepatocellular cancer. Epigenetics, 12(3), 215-225.
27. Picelli, S., Faridani, O. R., Björklund, Å. K., Winberg, G., Sagasser, S., & Sandberg, R. (2014). Full-length RNA-seq from single cells using Smart-seq2. Nature protocols, 9(1), 171.
28. Pertea, M., Kim, D., Pertea., G. M., Leek, J. T., &. Salzberg, S. L. (2016). Transcript-level expression analysis of RNA-seg experiments with HISAT, StringTie and Ballgown. Nature protocols, 11(9), 1650.
29. P Values, False Discovery Rate and q-values. (2019). Nonlinear Dynamics: A Walters Company. Retrieved from http://www.nonlinear.com/support/progenesis/comet/faq/v2.0/pq-values.aspx
30. Zheng, Z.-M. (2010). Viral Oncogenes, Noncoding RNAs, and RNA Splicing in Human Tumor Viruses. International Journal of Biological Sciences, 6(7), 730-755.
31. Cesarman, E., and Mesri, E. A. (2006). Pathogenesis of viral lymphomas. Cancer Treat. Res. 131, 49-88.
32. Kutok, J. L., & Wang, F. (2006). Spectrum of Epstein-Barr virus-associated diseases. Annu. Rev. Pathol. Mech. Dis., 1, 375-404.
33. Tsimbouri, P., Drotar, M. E., Coy. J. L., and Wilson, J. B. (2002). bcl-xL and RAG genes are induced and the response to IL-2 enhanced in ErnuEBNA-1 trans-genic mouse lymphocytes. Oncogene 21, 5182-51871.
34. Hanahan D., & Weinberg, R. A. (2011). Hallmarks of cancer: the next generation. cell, 144(5), 646-674.
35. Braf Gene—Genetics Home Reference—NIH. Retrieved from https://ghr.nlm.nih.gov/gene/BRAF#
36. Chalhoub, N., & Baker. S. J. (2009), PTEN and the PI3-Kinase Pathway in Cancer. Annual review of pathology, 4, 127.

37. Frenzel, A., Grespi, F., Chmelewskij, W., & Villunger, A. (2009). Bcl2 family proteins in carcinogenesis and the treatment of cancer. *Apoptosis,* 14(4), 584-596.
38. Xia, Y., Shen, S., & Verma, I. M. (2014). NF-κB, an active player in human cancers. *Cancer immunology research,* 2(9), 823-830.
39. Takashima,A., & Faller, D. V. (2013). Targeting the RAS oncogene. *Expert opinion on therapeutic targets,* 17(5), 507-531.
40. Zhang, C., Moore, L. M., Li, X., Yung, W. A., & Zhang, W. (2013). IDH1/2 mutations target a key hallmark of cancer by deregulating cellular metabolism in glioma. *Neuro-oncology,* 15(9), 1114-1126.
41. Akagi, K., Li, J., Broutian, T. R., Padilla-Nash, H., Xiao, W., Jiang, B., . . . & He, D. (2014). Genome-wide analysis of HPV integration in human cancers reveals recurrent, focal genomic instability. Genome research, 24(2), 185-199.
42. Jang, M., Kim, S. S., & Lee, J. (2013), Cancer cell metabolism: implications for therapeutic targets. *Experimental & molecular medicine,* 45(10), e45.
43. "Natural Killer Cells." Immunology. Retrieved from, https://www.immunology.org/public-information/bite-sized-immunology/cells/natural-killer-cells
44. Nishida, N., Yano, H., Nishida, T., Kamura, T., & Kojiro, M. (2006). Angiogenesis in cancer. *Vascular health and risk management,* 2(3), 213.
45. Nishida, N., Yano, H., Nishida, T., Kamura, T., & Kojiro, M. (2006). Angiogenesis in cancer. *Vascular health and risk management,* 2(3), 213.
CD4+ Cells. Immunology. Retrieved from, https://www.immunology.org/public-information/bitesized-immunology/cells/cd4-t-cells
46. Hlady, R. A., Sathyanarayan, A., Thompson, J. J., Zhou, D., Wu, Q., Pham, K., . . . & Robertson, K. D. (2019). Integrating the Epigenome to Identify Drivers of Hepatocellular Carcinoma. *Hepatology,* 69(2), 639-652.
47. ATCC. (2019). Cell Line Products. Available from: https://www.atcc.org/Products/Cells_and_Microorganisms.aspx
48. Illumina. (2018). Introduction to Targeted RNA Sequencing. Illumina Technologies. Retrieved from: https://www.illumina.com/techniques/sequencing/rna-sequencing/targeted-rna-seq.html
49. Bao, G., Rhee, W. J., & Tsourkas, A. (2009). Fluorescent Probes for Live-Cell RNA Detection. Annual Review of Biomedical Engineering, 11, 25-47. http://doi.org/10.1146/annurev-bioeng-061008-124920
50. Wang, Z., Gerstein, M., & Snyder, M. (2009). RNA-Seq: a revolutionary tool for transcriptomics. Nature reviews genetics, 10(1), 57.
51. Geneious. (2018). Features: Access all the Bioinformatics tools you need from one program. Geneious Biologics. Retrieved from: https://www.geneious.com/
52. Sigma Aldrich. (2018). Primer and Probe Design. Retrieved from: https://www.sigmaaldrich.com/content/dam/sigma-aldrich/docs/SAJ/Brochure/1/j_qper_techguide03.pdf
53. Nucleotide BLAST: Search Nucleotide Databases Using a Nucleotide Query." National Center for Biotechnology Information, U.S. National Library of Medicine, blast.ncbi.nlm.nih.gov/Blast.cgi?PAGE_TYPE=BlastSearch
54. Sigma Aldrich. (2018). Oligo Architect™ Online: Open Tool Design. Retrieved from: https://www.sigmaaldrich.com/technical-documents/articles/biology/oligoarchitect-online.html
55. Premier Biosoft. (2018). Multiplex PCR. Premier Biosoft: Accelerating Research in Life Sciences. http://www.premierbiosoft.com/tech_notes/multiplex-per.html
56. Thul, P. J., Åkesson, L., Mandessian, D., Bäckström, A., Danielsson, F., Gnann, C., . . . & Winsnes, C. (2017). An image-based subcellular map of the human proteome. In Molecular Biology of the Cell (Vol. 28). American Society for Cell Biology.
57. Untergasser, A., Cutcutache, I., Koressaar, T., Ye, J., Faircloth, B. C., Remm, M., & Rozen, S. G. (2012). Primer3—new capabilities and interfaces. Nucleic Acids Research, 40(15), e115. http://doi.org/10.1093/nar/gks596
58. Koressaar, T., & Remm, M. (2007). Enhancements and modifications of primer design program Primer3. Bioinformatics, 23(10), 1289-1291.
59. Lau et al (2017) The Cancer Genomics Cloud: Collaborative, Reproducible, and Democratized—A New Paradigm in Large-Scale Computational Research. Cancer Res. 77(21):e3-e6. doi: 10.1158/0008-5472.CAN-17-0387.
60. Probe [Internet]. Bethesda (Md.): National Library of Medicine (US), National Center for Biotechnology Information; 2004—[cited 2019 Jul. 4]. Available from: https://www.ncbi.nlm.nih.gov/gene/

What is claimed is:

1. A method for treating a tumorigenic phenotype of a liver of a subject, comprising:
   (a) isolating cell-free deoxyribonucleic acid (cfDNA) molecules obtained or derived from a blood sample of the subject, wherein the subject has been diagnosed with chronic hepatitis, and wherein the subject has not been diagnosed with a liver cancer;
   (b) subjecting the cfDNA molecules to ten-eleven translocation (TET)-associated sequencing, wherein the TET-associated sequencing comprises:
      (i) using a TET enzyme to oxidize 5-methylcytosine (5-mC) residues and 5-hydroxymethylcytosine (5-hmC) residues of the cfDNA molecules, thereby producing TET-converted cfDNA molecules, and
      (ii) sequencing the TET-converted cfDNA molecules to produce a set of cfDNA methylation sequencing reads;
   (c) processing the set of cfDNA methylation sequencing reads to determine a liver-specific methylation pattern of the cfDNA molecules across a set of liver-specific differentially methylated genomic regions,
      wherein the set of liver-specific differentially methylated genomic regions comprises at least a portion of oncogenes that are differentially methylated during induction of liver cancer tumorigenesis,
      wherein the processing comprises distinguishing between 5-mC and 5-hmC residues of the cfDNA molecules and cytosine residues of the cfDNA molecules;
   (d) determining a presence of a tumorigenic phenotype of the liver of the subject, based at least in part on the determined liver-specific methylation pattern, wherein the tumorigenic phenotype comprises induction of liver cancer tumorigenesis; and
   (e) administering a treatment to the subject to treat the tumorigenic phenotype of the liver of the subject, wherein the treatment comprises a Hepatitis C virus inhibitor, a chemotherapy, a radiation therapy, or a liver transplant.

2. The method of claim 1, further comprising determining the liver-specific methylation pattern of the cfDNA molecules at least in part by measuring a level of methylation in the cfDNA molecules relative to a reference level of methylation.

3. The method of claim 2, wherein the tumorigenic phenotype of the liver of the subject is determined based at least in part on whether the level of methylation has a log change in average methylation ratio $\beta$ of greater than 0.2 relative to the reference level of methylation.

4. The method of claim 1, wherein the liver-specific differentially methylated genomic regions comprise a member selected from the group consisting of ALB, HP, FGB, FGG, and SERPINA1.

5. The method of claim 1, wherein the blood sample has a volume of from about 50 nanoliters to about 5 milliliters.

6. The method of claim 1, wherein the cfDNA molecules are obtained or derived from a plasma sample.

7. The method of claim 1, wherein the liver cancer is hepatocellular carcinoma.

8. The method of claim 1, wherein the TET enzyme comprises a TET1 enzyme.

9. The method of claim 1, wherein the TET-associated sequencing is TET-associated bisulfite sequencing.

10. The method of claim 1, further comprising:
   assaying cell-free ribonucleic acid (cfRNA) molecules obtained or derived from the blood sample, to determine a gene expression pattern of the cfRNA molecules across a set of differentially expressed genomic regions, wherein the set of differentially expressed genomic regions are differentially expressed during induction of liver cancer tumorigenesis, and wherein the determining in (d) is further based at least in part on the determined gene expression pattern.

11. The method of claim 10, wherein the assaying comprises RNA sequencing.

12. The method of claim 10, wherein the set of differentially expressed genomic regions comprises a member selected from the group consisting of GBK2, NDUFB10, PARL, ZW10, Y1F1B, UPB1, TBC1D10C, GNA11, IQSEC1, COL15A1, and SLC30A6.

13. The method of claim 1, wherein the treatment comprises the Hepatitis C virus inhibitor.

14. The method of claim 1, wherein the treatment comprises the chemotherapy.

15. The method of claim 1, wherein the treatment comprises the radiation therapy.

16. The method of claim 1, wherein the treatment comprises the liver transplant.

* * * * *